＊ ＊ ＊

(12) United States Patent
Chen et al.

(10) Patent No.: US 11,591,580 B2
(45) Date of Patent: Feb. 28, 2023

(54) K85 MUTATION-CONTAINING PLANT EPSPS MUTANT, AND ENCODING GENE AND APPLICATION THEREOF

(71) Applicant: GEVOTO LLC, Sichuan (CN)

(72) Inventors: Rong Chen, Sichuan (CN); Longqun Deng, Sichuan (CN); Qingjiang Hou, Sichuan (CN); Yuangen Lu, Sichuan (CN); Qian Ou, Sichuan (CN); Xiaorong Feng, Sichuan (CN); Ling Li, Sichuan (CN); Xin Huang, Sichuan (CN); Nanfei Xu, Sichuan (CN)

(73) Assignee: GEVOTO LLC, Sichuan (CN)

( * ) Notice: Subject to any disclaimer, the term of this patent is extended or adjusted under 35 U.S.C. 154(b) by 263 days.

(21) Appl. No.: 16/761,146

(22) PCT Filed: Dec. 14, 2018

(86) PCT No.: PCT/CN2018/121331
§ 371 (c)(1),
(2) Date: May 1, 2020

(87) PCT Pub. No.: WO2019/086051
PCT Pub. Date: May 9, 2019

(65) Prior Publication Data
US 2020/0318085 A1    Oct. 8, 2020

(30) Foreign Application Priority Data

Nov. 2, 2017   (CN) .......................... 201711062251.2
Sep. 13, 2018  (CN) .......................... 201811070065.8

(51) Int. Cl.
*C12N 9/10*    (2006.01)
*C12N 15/82*   (2006.01)

(52) U.S. Cl.
CPC ....... *C12N 9/1092* (2013.01); *C12N 15/8275* (2013.01); *C12Y 205/01019* (2013.01)

(58) Field of Classification Search
None
See application file for complete search history.

(56) References Cited

U.S. PATENT DOCUMENTS 6,566,587 B1 *  5/2003  Lebrun ................ C12N 9/1092
                                                536/23.6

FOREIGN PATENT DOCUMENTS

CN    1810962 A     8/2006
CN    106636025 A   5/2017

OTHER PUBLICATIONS

Haghani et al. (2008) Biochim Biophys Acta 1784:1167-75.*
First Office Action issued in CN 201811070065.8, with English-language translation, dated Jun. 5, 2019.
(Continued)

*Primary Examiner* — Matthew R Keogh
*Assistant Examiner* — Rebecca Stephens
(74) *Attorney, Agent, or Firm* — Hogan Lovells US LLP

(57) ABSTRACT

The invention provides a plant EPSPS mutant (i.e. 5-enolpyruvylshikimate-3-phosphate synthase mutant), which is derived from plant, and has glyphosate resistance after mutation. Also provided is an encoding gene, which can encode the above plant EPSPS mutant; and a vector containing the above encoding gene; and a cell containing the above vector. Further provided are uses of the above plant EPSPS mutant.

7 Claims, 3 Drawing Sheets
Specification includes a Sequence Listing.

Ec-EPSPS WT NALTALGVSYTLSADRTRCEIIGNGGPLH----AEGALELFLGNAGTAMRPLAAA 105

Os-EPSPS M EALKALGLSVEADKVAKRAVVVGCGGKFPVEKDAIEEVQLFLGNAATAMRSLTAA 120

Os-EPSPS WT EALKALGLSVEADKVAKRAVVVGCGGKFPVEKDAKEEVQLFLGNAGTAMRPLTAA 120

(56) References Cited

OTHER PUBLICATIONS

Second Office Action issued in CN 201811070065.8, with English-language translation, dated Aug. 12, 2019.
International Search Report dated Mar. 7, 2019 in International Application No. PCT/CN2018/121331, with English-language translation.
First Search Report of Priority Document No. 201811070065.8.
Written Opinion dated Jul. 3, 2019 in PCT/CN2018/121331.
CA office action dated Apr. 21, 2021 from CA application serial No. 3,081,378.
Gong, et al. Camptotheca Acuminata 5-Enolpyruvylshikimate 3-Phosphate Synthase (EPSPS) mRNA, Complete cds, GenBank AY639815.1, Aug. 15, 2006.

\* cited by examiner

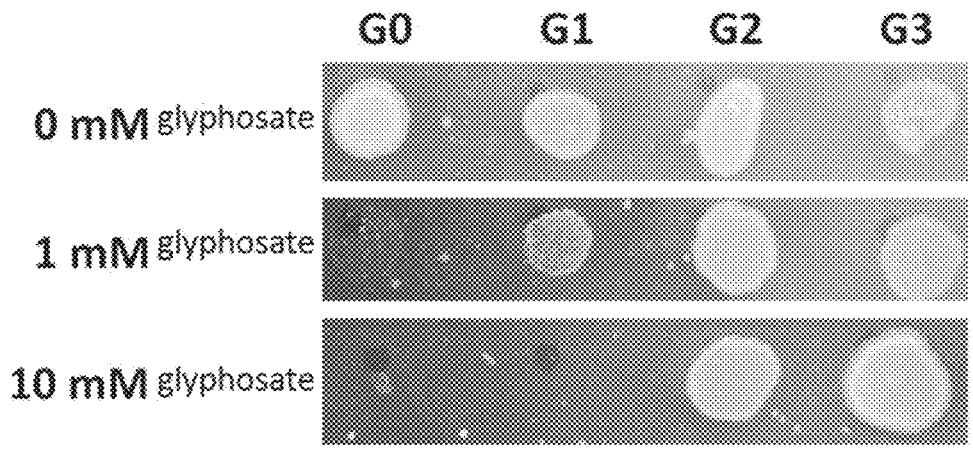
FIG. 3
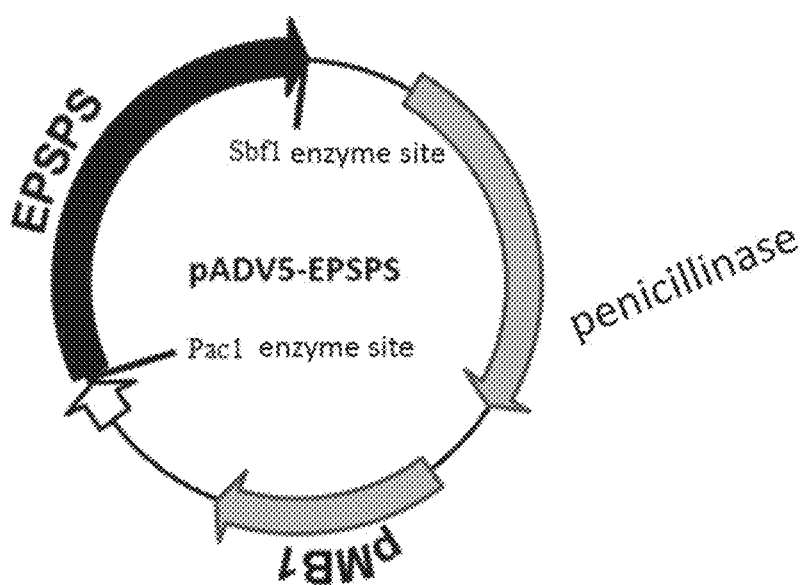
FIG. 4
```
Ec-EPSPS WT  NALTALGVSYTLSADRTRCEIIGNGGPLH----AEGALELFLGNAGTAMRPLAAA 105
Os-EPSPS M   EALKALGLSVEADKVAKRAVVVGCGGKFPVEKDAIEEVQLFLGNAATAMRSLTAA 120
Os-EPSPS WT  EALKALGLSVEADKVAKRAVVVGCGGKFPVEKDAKEEVQLFLGNAGTAMRPLTAA 120
```
FIG. 5

```
Ec-EPSPS WT  NALTALGVSYTLSADRTRCEIIGNGGPLH----AEGALELFLGNAGTAMRPLAAA 105
Zm-EPSPS M   GALRTLGLSVEADKAAKRAVVVGCGGKFPVE-DSIEEVQLFLGNAATAMRSLTAA 114
Zm-EPSPS WT  GALRTLGLSVEADKAAKRAVVVGCGGKFPVE-DSKEEVQLFLGNAGTAMRPLTAA 114

Ec-EPSPS WT  VSSQFLTALLMTAPLAPEDTVIRIKGDLVSKPYIDITLNLMKTFGVEIEN-QHYQ 221
Zm-EPSPS M   ISSQYLSALLMAAPLALGDVEIEIIDRLISIPYVEMTLRLMERFGVKAEHSDSWD 235
Zm-EPSPS WT  ISSQYLSALLMAAPLALGDVEIEIIDKLISIPYVEMTLRLMERFGVKAEHSDSWD 235
```

FIG. 6

```
Ec-EPSPS WT  NALTALGVSYTLSADRTRCEIIGNGGPLH----AEGALELFLGNAGTAMRPLAAA 105
Gm-EPSPS M   GALRTLGLRVEDDQTTKQAIVEGCGGLFPTIKESTDEINLFLGNAGTAMRSLTAA 118
Gm-EPSPS WT  GALRTLGLRVEDDQTTKQAIVEGCGGLFPTIKESKDEINLFLGNAGTAMRPLTAA 118
```

FIG. 7

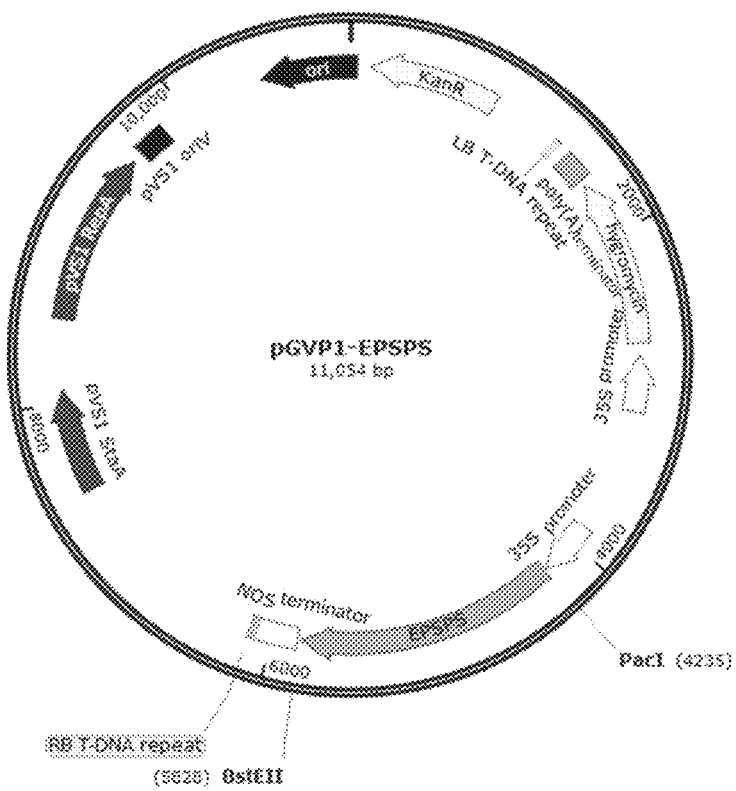

FIG. 8

SEQUENCE LISTING

```
<160> NUMBER OF SEQ ID NOS: 39

<210> SEQ ID NO 1
<211> LENGTH: 1365
<212> TYPE: DNA
<213> ORGANISM: Oryza sativa

<400> SEQUENCE: 1
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga gggcacaaca gtggtggaca acttgctgaa cagtgaggat     180
gttcactaca tgcttgaggc cctgaaagcc ctcgggctct ctgtggaagc agataaagtt     240
gcaaaaagag ctgtagtcgt tggctgtggt ggcaagtttc ctgttgagaa ggatgcgaaa     300
gaggaagtgc aactcttctt ggggaacgct ggaactgcaa tgcgaccatt gacagcagcc     360
gtgactgctg ctggtggaaa tgcaacttat gtgcttgatg gagtgccacg aatgagggag     420
agaccgattg gtgacttggt tgtcgggttg aaacaacttg gtgcggatgt cgactgtttc     480
cttggcactg aatgcccacc tgttcgtgtc aagggaattg gaggacttcc tggtggcaag     540
gttaagctct ctggttccat cagcagtcag tacttgagtg ccttgctgat ggctgctcct     600
ttggcccttg gggatgtgga gatcgaaatc attgacaaac taatctccat tccttacgtt     660
gaaatgacat tgagattgat ggagcgtttt ggtgtgaagg cagagcattc tgatagttgg     720
gacagattct atattaaggg agggcagaag tacaaatctc ctggaaatgc ctatgttgaa     780
ggtgatgcct caagcgcgag ctatttcttg gctggtgctg caatcactgg aggcactgtg     840
acagttcaag gttgtggtac gaccagtttg cagggtgatg tcaaatttgc tgaggtactt     900
gagatgatgg gagcaaaggt tacatggact gacaccagtg taaccgtaac tggtccacca     960
cgtgagcctt atgggaagaa acacctgaaa gctgttgatg tcaacatgaa caaaatgcct    1020
gatgttgcca tgacccttgc cgttgttgca ctcttcgctg atggtccaac tgctatcaga    1080
gatgtggctt cctggagagt aaaggaaacc gaaaggatgg ttgcaattcg gaccgagcta    1140
acaaagctgg gagcatcggt tgaagaaggt cctgactact gcatcatcac ccccaccggag    1200 aagctgaaca tcacggcaat cgacacctac gatgatcaca ggatggccat ggccttctcc    1260
ctcgctgcct gcgccgacgt gcccgtgacg atcagggacc ctggttgcac ccgcaagacc    1320
ttccccaact acttcgacgt tctaagcact ttcgtcagga actga                    1365
```

```
<210> SEQ ID NO 2
<211> LENGTH: 454
<212> TYPE: PRT
<213> ORGANISM: Oryza sativa

<400> SEQUENCE: 2

Met Ala Ser Asn Ala Ala Ala Ala Lys Ala Glu Ile Val
1               5                   10                  15

Leu Gln Pro Ile Arg Glu Ile Ser Gly Ala Val Gln Leu Pro Gly Ser
                20                  25                  30

Lys Ser Leu Ser Asn Arg Ile Leu Leu Leu Ser Ala Leu Ser Glu Gly
            35                  40                  45

Thr Thr Val Val Asp Asn Leu Leu Asn Ser Glu Asp Val His Tyr Met
50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Gly Thr
                100                 105                 110

Ala Met Arg Pro Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
        130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gln Lys Tyr Lys Ser Pro Gly Asn
                245                 250                 255

Ala Tyr Val Glu Gly Asp Ala Ser Ser Ala Ser Tyr Phe Leu Ala Gly
                260                 265                 270

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
        290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
                340                 345                 350

Ala Asp Gly Pro Thr Ala Ile Arg Asp Val Ala Ser Trp Arg Val Lys
            355                 360                 365

Glu Thr Glu Arg Met Val Ala Ile Arg Thr Glu Leu Thr Lys Leu Gly
        370                 375                 380
```

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
            405                 410                 415

Met Ala Phe Ser Leu Ala Ala Cys Ala Asp Val Pro Val Thr Ile Arg
        420                 425                 430

Asp Pro Gly Cys Thr Arg Lys Thr Phe Pro Asn Tyr Phe Asp Val Leu
    435                 440                 445

Ser Thr Phe Val Arg Asn
    450

<210> SEQ ID NO 3
<211> LENGTH: 1365
<212> TYPE: DNA
<213> ORGANISM: Artificial Sequence
<220> FEATURE:
<223> OTHER INFORMATION: Encoding Oryza sativa EPSPS mutant with
      mutation K100(85)I

<400> SEQUENCE: 3
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga ggcacaaca gtggtggaca acttgctgaa cagtgaggat      180
gttcactaca tgcttgaggc cctgaaagcc ctcgggctct ctgtggaagc agataaagtt     240
gcaaaagag ctgtagtcgt tggctgtggt ggcaagtttc ctgttgagaa ggatgcgatt      300
gaggaagtgc aactcttctt ggggaacgct ggaactgcaa tgcgaccatt gacagcagcc     360
gtgactgctg ctggtggaaa tgcaacttat gtgcttgatg gagtgccacg aatgagggag     420
agaccgattg gtgacttggt tgtcgggttg aaacaacttg gtgcggatgt cgactgtttc     480
cttggcactg aatgcccacc tgttcgtgtc aagggaattg aggacttcc tggtggcaag     540
gttaagctct ctggttccat cagcagtcag tacttgagtg ccttgctgat ggctgctcct     600
ttggccttg ggatgtgga gatcgaaatc attgacaaac taatctccat tccttacgtt      660
gaaatgacat tgagattgat ggagcgtttt ggtgtgaagg cagagcattc tgatagttgg     720
gacagattct atattaaggg agggcagaag tacaaatctc ctggaaatgc ctatgttgaa     780
ggtgatgcct caagcgcgag ctatttcttg gctggtgctg caatcactgg aggcactgtg     840
acagttcaag gttgtggtac gaccagtttg cagggtgatg tcaaatttgc tgaggtactt     900
gagatgatgg gagcaaaggt tacatggact gacaccagtg taaccgtaac tggtccacca     960
cgtgagcctt atgggaagaa acacctgaaa gctgttgatg tcaacatgaa caaaatgcct    1020
gatgttgcca tgaccctgc cgttgttgca ctcttcgctg atggtccaac tgctatcaga    1080
gatgtggctt cctggagagt aaaggaaacc gaaaggatgg ttgcaattcg gaccgagcta    1140
acaaagctgg gagcatcggt tgaagaaggt cctgactact gcatcatcac cccaccggag    1200
aagctgaaca tcacggcaat cgacacctac gatgatcaca ggatggccat ggccttctcc    1260
ctcgctgcct gcgccgacgt gcccgtgacg atcagggacc ctggttgcac ccgcaagacc    1320
ttccccaact acttcgacgt tctaagcact ttcgtcagga actga                    1365

<210> SEQ ID NO 4
<211> LENGTH: 454
<212> TYPE: PRT
<213> ORGANISM: Artificial Sequence
<220> FEATURE:
<223> OTHER INFORMATION: Oryza sativa EPSPS mutant with mutation
     K100(85)I

<400> SEQUENCE: 4

```
Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Ile Glu Glu Val Gln Leu Phe Leu Gly Asn Ala Gly Thr
            100                 105                 110

Ala Met Arg Pro Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380

Ala Ser Val Glu Glu Gly Pro Asp Tyr Cys Ile Ile Thr Pro Pro Glu
```

```
                385                 390                 395                 400
Lys Leu Asn Ile Thr Ala Ile Asp Thr Tyr Asp Asp His Arg Met Ala
                    405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450

<210> SEQ ID NO 5
<211> LENGTH: 1365
<212> TYPE: DNA
<213> ORGANISM: Artificial Sequence
<220> FEATURE:
<223> OTHER INFORMATION: Encoding Oryza sativa EPSPS mutant with
      mutations G111(96)A and P116(101)S

<400> SEQUENCE: 5
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga gggcacaaca gtggtggaca acttgctgaa cagtgaggat     180
gttcactaca tgcttgaggc cctgaaagcc ctcgggctct ctgtggaagc agataaagtt     240
gcaaaaagag ctgtagtcgt tggctgtggt ggcaagtttc ctgttgagaa ggatgcgaaa     300
gaggaagtgc aactcttctt ggggaacgct gcgactgcaa tgcgatcctt gacagcagcc     360
gtgactgctg ctggtggaaa tgcaacttat gtgcttgatg gagtgccacg aatgagggag     420
agaccgattg gtgacttggt tgtcgggttg aaacaacttg gtgcggatgt cgactgtttc     480
cttggcactg aatgcccacc tgttcgtgtc aagggaattg gaggacttcc tggtggcaag     540
gttaagctct ctggttccat cagcagtcag tacttgagtg ccttgctgat ggctgctcct     600
ttggcccttg gggatgtgga gatcgaaatc attgacaaac taatctccat tccttacgtt     660
gaaatgacat tgagattgat ggagcgtttt ggtgtgaagg cagagcattc tgatagttgg     720
gacagattct atattaaggg agggcagaag tacaaatctc tggaaatgc ctatgttgaa     780 ggtgatgcct caagcgcgag ctatttcttg gctggtgctg caatcactgg aggcactgtg     840
acagttcaag ttgtggtac gaccagtttg cagggtgatg tcaaatttgc tgaggtactt     900
gagatgatgg agcaaaggt tacatggact gacaccagtg taaccgtaac tggtccacca     960
cgtgagcctt atgggaagaa acacctgaaa gctgttgatg tcaacatgaa caaaatgcct    1020
gatgttgcca tgaccttgc cgttgttgca ctcttcgctg atggtccaac tgctatcaga    1080
gatgtggctt cctggagagt aaaggaaacc gaaaggatgg ttgcaattcg gaccgagcta    1140
acaaagctgg gagcatcggt tgaagaaggt cctgactact gcatcatcac cccaccggag    1200
aagctgaaca tcacggcaat cgacacctac gatgatcaca ggatggccat ggccttctcc    1260
ctcgctgcct gcgccgacgt gcccgtgacg atcagggacc ctggttgcac ccgcaagacc    1320
ttccccaact acttcgacgt tctaagcact ttcgtcagga actga                   1365

<210> SEQ ID NO 6
<211> LENGTH: 454
<212> TYPE: PRT
<213> ORGANISM: Artificial Sequence
<220> FEATURE:
<223> OTHER INFORMATION: Oryza sativa EPSPS mutant with mutations
      G111(96)A and P116(101)S
```

<400> SEQUENCE: 6

Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Ser Ala Leu Ser Glu Gly
                35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Gly Cys Gly Gly Lys Phe Pro Val Glu
                85                  90                  95

Lys Asp Ala Lys Glu Glu Val Gln Leu Phe Leu Gly Asn Ala Ala Thr
            100                 105                 110

Ala Met Arg Ser Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
    195                 200                 205

Glu Ile Ile Asp Lys Leu Ile Ser Ile Pro Tyr Val Glu Met Thr Leu
210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
            355                 360                 365

Glu Thr Glu Arg Met Val Ala Ile Arg Thr Glu Leu Thr Lys Leu Gly
    370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala 405                 410                 415
Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
            435                 440                 445

Ser Thr Phe Val Arg Asn
    450

<210> SEQ ID NO 7
<211> LENGTH: 1365
<212> TYPE: DNA
<213> ORGANISM: Artificial Sequence
<220> FEATURE:
<223> OTHER INFORMATION: Encoding Oryza sativa EPSPS mutant with
      mutations K100(85)I, G111(96)A and P116(101)S

<400> SEQUENCE: 7
atggcgtcca acgccgcggc tgcggcggcg aaggcggagg agatcgtgct ccagcccatc      60
agggagatct ccggggcggt tcagctgcca gggtccaagt cgctctccaa caggatcctc     120
ctcctctccg ccctctccga gggcacaaca gtggtggaca acttgctgaa cagtgaggat     180
gttcactaca tgcttgaggc cctgaaagcc ctcgggctct ctgtggaagc agataaagtt     240
gcaaaaagag ctgtagtcgt tggctgtggt ggcaagtttc ctgttgagaa ggatgcgatt     300
gaggaagtgc aactcttctt ggggaacgct gcgactgcaa tgcgatcctt gacagcagcc     360
gtgactgctg ctggtggaaa tgcaacttat gtgcttgatg agtgccacg aatgagggag     420 agaccgattg tgacttggt tgtcgggttg aaacaacttg gtgcggatgt cgactgtttc     480
cttggcactg aatgcccacc tgttcgtgtc aagggaattg aggacttcc tggtggcaag     540 gttaagctct ctggttccat cagcagtcag tacttgagtg ccttgctgat ggctgctcct     600
ttggcccttg ggatgtgga tcgaaatc attgacaaac taatctccat tccttacgtt     660
gaaatgacat tgagattgat ggagcgtttt ggtgtgaagg cagagcattc tgatagttgg     720
gacagattct atattaaggg agggcagaag tacaaatctc ctggaaatgc ctatgttgaa     780
ggtgatgcct caagcgcgag ctatttcttg gctggtgctg caatcactgg aggcactgtg     840
acagttcaag ttgtggtac gaccagtttg cagggtgatg tcaaatttgc tgaggtactt     900
gagatgatgg gagcaaaggt tacatggact gacaccagtg taaccgtaac tggtccacca     960
cgtgagcctt atgggaagaa acacctgaaa gctgttgatg tcaacatgaa caaaatgcct    1020
gatgttgcca tgacccttgc cgttgttgca ctcttcgctg atggtccaac tgctatcaga    1080
gatgtggctt cctggagagt aaaggaaacc gaaaggatgg ttgcaattcg gaccgagcta    1140
acaaagctgg gagcatcggt tgaagaaggt cctgactact gcatcatcac cccaccggag    1200
aagctgaaca tcacggcaat cgacacctac gatgatcaca ggatggccat ggccttctcc    1260
ctcgctgcct gcgccgacgt gcccgtgacg atcagggacc ctggttgcac ccgcaagacc    1320
ttccccaact acttcgacgt tctaagcact ttcgtcagga actga                    1365

<210> SEQ ID NO 8
<211> LENGTH: 454
<212> TYPE: PRT
<213> ORGANISM: Artificial Sequence
<220> FEATURE:
<223> OTHER INFORMATION: Oryza sativa EPSPS mutant with mutations
      K100(85)I, G111(96)A and P116(101)S

<400> SEQUENCE: 8

```
Met Ala Ser Asn Ala Ala Ala Ala Lys Ala Glu Glu Ile Val
1               5                   10                  15
Leu Gln Pro Ile Arg Glu Ile Ser Gly Ala Val Gln Leu Pro Gly Ser
            20                  25                  30
Lys Ser Leu Ser Asn Arg Ile Leu Leu Ser Ala Leu Ser Glu Gly
        35                  40                  45
Thr Thr Val Val Asp Asn Leu Leu Asn Ser Glu Asp Val His Tyr Met
    50                  55                  60
Leu Glu Ala Leu Lys Ala Leu Gly Leu Ser Val Glu Ala Asp Lys Val
65                  70                  75                  80
Ala Lys Arg Ala Val Val Gly Cys Gly Gly Lys Phe Pro Val Glu
                85                  90                  95
Lys Asp Ala Ile Glu Glu Val Gln Leu Phe Leu Gly Asn Ala Ala Thr
            100                 105                 110
Ala Met Arg Ser Leu Thr Ala Ala Val Thr Ala Ala Gly Gly Asn Ala
        115                 120                 125
Thr Tyr Val Leu Asp Gly Val Pro Arg Met Arg Glu Arg Pro Ile Gly
    130                 135                 140
Asp Leu Val Val Gly Leu Lys Gln Leu Gly Ala Asp Val Asp Cys Phe
145                 150                 155                 160
Leu Gly Thr Glu Cys Pro Pro Val Arg Val Lys Gly Ile Gly Leu
                165                 170                 175
Pro Gly Gly Lys Val Lys Leu Ser Gly Ser Ile Ser Ser Gln Tyr Leu
            180                 185                 190
Ser Ala Leu Leu Met Ala Ala Pro Leu Ala Leu Gly Asp Val Glu Ile
        195                 200                 205
Glu Ile Ile Asp Lys Leu Ile Ser Ile Pro Tyr Val Glu Met Thr Leu
    210                 215                 220
Arg Leu Met Glu Arg Phe Gly Val Lys Ala Glu His Ser Asp Ser Trp
225                 230                 235                 240
Asp Arg Phe Tyr Ile Lys Gly Gly Gln Lys Tyr Lys Ser Pro Gly Asn
                245                 250                 255
Ala Tyr Val Glu Gly Asp Ala Ser Ser Ala Ser Tyr Phe Leu Ala Gly
            260                 265                 270
Ala Ala Ile Thr Gly Gly Thr Val Thr Val Gln Gly Cys Gly Thr Thr
        275                 280                 285
Ser Leu Gln Gly Asp Val Lys Phe Ala Glu Val Leu Glu Met Met Gly
    290                 295                 300
Ala Lys Val Thr Trp Thr Asp Thr Ser Val Thr Val Thr Gly Pro Pro
305                 310                 315                 320
Arg Glu Pro Tyr Gly Lys Lys His Leu Lys Ala Val Asp Val Asn Met
                325                 330                 335
Asn Lys Met Pro Asp Val Ala Met Thr Leu Ala Val Val Ala Leu Phe
            340                 345                 350
Ala Asp Gly Pro Thr Ala Ile Arg Asp Val Ala Ser Trp Arg Val Lys
        355                 360                 365
Glu Thr Glu Arg Met Val Ala Ile Arg Thr Glu Leu Thr Lys Leu Gly
    370                 375                 380
Ala Ser Val Glu Glu Gly Pro Asp Tyr Cys Ile Ile Thr Pro Pro Glu
385                 390                 395                 400
Lys Leu Asn Ile Thr Ala Ile Asp Thr Tyr Asp Asp His Arg Met Ala
                405                 410                 415
Met Ala Phe Ser Leu Ala Ala Cys Ala Asp Val Pro Val Thr Ile Arg
```

```
                420            425            430
Asp Pro Gly Cys Thr Arg Lys Thr Phe Pro Asn Tyr Phe Asp Val Leu
        435                440                445

Ser Thr Phe Val Arg Asn
        450

<210> SEQ ID NO 9
<211> LENGTH: 1347
<212> TYPE: DNA
<213> ORGANISM: Zea mays

<400> SEQUENCE: 9
atggcggtgc aggcgggtgc cgaggagatc gtgctgcagc ccatcaagga gatctccggc      60
accgtcaagc tgccggggtc caagtcgctt tccaaccgga tcctcctgct cgccgccctg     120 tccgaggga  caacagtggt tgataacctg ttgaacagtg aggatgtcca ctacatgctc     180
ggggccttga ggactcttgg tctctctgtc gaagcggaca agctgccaa  aagagctgta     240 gttgttggct gtggtggaaa gttcccagtt gaggattcta agaggaagt  gcagctcttc     300 ttggggaatg ctggaactgc aatgcggcca ttgacagcag ctgttactgc tgctggtgga     360
aatgcaactt acgtgcttga tggagtacca agaatgaggg agagacccat ggcgacttg     420 gttgtcggat tgaagcagct tggtgcagat gttgattgtt ccttggcac  tgactgccca     480 cctgttcgtg tcaatggaat cggagggcta cctggtggca aggtcaagct gtctggctcc     540
atcagcagtc agtacttgag tgccttgctg atggctgctc ctttggctct ggggatgtg     600 gagattgaaa tcattgataa attaatctcc attccctacg tcgaaatgac attgagattg     660
atggagcgtt ttggtgtgaa agcagagcat tctgatagct gggacagatt ctacattaag     720
ggaggtcaaa aatacaagtc ccctaaaaat gcctatgttg aaggtgatgc ctcaagcgca     780
agctatttct tggctggtgc tgcaattact ggagggactg tgactgtgga aggttgtggc     840
accaccagtt tgcagggtga tgtgaagttt gctgaggtac tggagatgat gggagcgaag     900
gttacatgga ccgagactag cgtaactgtt actggcccac cgcgggagcc atttgggagg     960
aaacacctca aggcgattga tgtcaacatg aacaagatgc tgatgtcgc  catgactctt    1020 gctgtggttg ccctctttgc cgatggcccg acagccatca gagacgtggc ttcctggaga    1080
gtaaaggaga ccgagaggat ggttgcgatc cggacggagc taaccaagct gggagcatct    1140
gttgaggaag gccggactac tgcatcatc  acgccgccgg agaagctgaa cgtgacggcg    1200
atcgacacgt acgacgacca caggatggcc atggccttct cccttgccgc ctgtgccgag    1260
gtccccgtga ccatccggga ccctgggtgc acccggaaga ccttccccga ctacttcgat    1320
gtgctgagca ctttcgtcaa gaattaa                                        1347

<210> SEQ ID NO 10
<211> LENGTH: 448
<212> TYPE: PRT
<213> ORGANISM: Zea mays

<400> SEQUENCE: 10

Met Ala Val Gln Ala Gly Ala Glu Glu Ile Val Leu Gln Pro Ile Lys
1               5                  10                  15

Glu Ile Ser Gly Thr Val Lys Leu Pro Gly Ser Lys Ser Leu Ser Asn
            20                  25                  30

Arg Ile Leu Leu Leu Ala Ala Leu Ser Glu Gly Thr Thr Val Val Asp
        35                  40                  45
```

Asn Leu Leu Asn Ser Glu Asp Val His Tyr Met Leu Gly Ala Leu Arg
 50                  55                  60

Thr Leu Gly Leu Ser Val Glu Ala Asp Lys Ala Ala Lys Arg Ala Val
 65                  70                  75                  80

Val Val Gly Cys Gly Gly Lys Phe Pro Val Glu Asp Ser Lys Glu Glu
                 85                  90                  95

Val Gln Leu Phe Leu Gly Asn Ala Gly Thr Ala Met Arg Pro Leu Thr
            100                 105                 110

Ala Ala Val Thr Ala Ala Gly Gly Asn Ala Thr Tyr Val Leu Asp Gly
            115                 120                 125

Val Pro Arg Met Arg Glu Arg Pro Ile Gly Asp Leu Val Val Gly Leu
        130                 135                 140

Lys Gln Leu Gly Ala Asp Val Asp Cys Phe Leu Gly Thr Asp Cys Pro
145                 150                 155                 160

Pro Val Arg Val Asn Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Ile Asp Lys Leu
        195                 200                 205

Ile Ser Ile Pro Tyr Val Glu Met Thr Leu Arg Leu Met Glu Arg Phe
210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
        435                 440                 445

<210> SEQ ID NO 11
<211> LENGTH: 1347
<212> TYPE: DNA

<213> ORGANISM: Artificial Sequence
<220> FEATURE:
<223> OTHER INFORMATION: Encoding Zea mays EPSPS mutant with mutation K94(85)I

<400> SEQUENCE: 11

```
atggcggtgc aggcgggtgc cgaggagatc gtgctgcagc ccatcaagga gatctccggc    60
accgtcaagc tgccggggtc caagtcgctt ccaaccgga tcctcctgct cgccgccctg    120
tccgagggga caacagtggt tgataacctg ttgaacagtg aggatgtcca ctacatgctc    180
ggggccttga ggactcttgg tctctctgtc gaagcggaca agctgccaa agagctgta    240
gttgttggct gtggtggaaa gttcccagtt gaggattcta tagaggaagt gcagctcttc    300
ttggggaatg ctggaactgc aatgcggcca ttgacagcag ctgttactgc tgctggtgga    360
aatgcaactt acgtgcttga tggagtacca agaatgaggg agagacccat ggcgacttg    420
gttgtcggat tgaagcagct tggtgcagat gttgattgtt ccttggcac tgactgccca    480
cctgttcgtg tcaatggaat cggagggcta cctggtggca aggtcaagct gtctggctcc    540
atcagcagtc agtacttgag tgccttgctg atggctgctc ctttggctct tggggatgtg    600
gagattgaaa tcattgataa attaatctcc attccctacg tcgaaatgac attgagattg    660
atggagcgtt ttggtgtgaa agcagagcat tctgatagct gggacagatt ctacattaag    720
ggaggtcaaa aatacaagtc ccctaaaaat gcctatgttg aaggtgatgc ctcaagcgca    780
agctatttct tggctggtgc tgcaattact ggagggactg tgactgtgga aggttgtggc    840
accaccagtt tgcagggtga tgtgaagttt gctgaggtac tggagatgat gggagcgaag    900
gttacatgga ccgagactag cgtaactgtt actggcccac cgcgggagcc atttggagg    960
aaacacctca aggcgattga tgtcaacatg aacaagatgc ctgatgtcgc catgactctt    1020
gctgtggttg ccctctttgc cgatggcccg acagccatca gagacgtggc ttcctggaga    1080
gtaaaggaga ccgagaggat ggttgcgatc cggacggagc taaccaagct gggagcatct    1140
gttgaggaag ggccggacta ctgcatcatc acgccgccgg agaagctgaa cgtgacggcg    1200
atcgacacgt acgacgacca caggatggcc atggccttct cccttgccgc ctgtgccgag    1260
gtccccgtga ccatccggga ccctgggtgc acccggaaga ccttccccga ctacttcgat    1320
gtgctgagca ctttcgtcaa gaattaa                                       1347
```

<210> SEQ ID NO 12
<211> LENGTH: 448
<212> TYPE: PRT
<213> ORGANISM: Artificial Sequence
<220> FEATURE:
<223> OTHER INFORMATION: Zea mays EPSPS mutant with mutation K94(85)I

<400> SEQUENCE: 12

```
Met Ala Val Gln Ala Gly Ala Glu Glu Ile Val Leu Gln Pro Ile Lys
  1               5                  10                  15

Glu Ile Ser Gly Thr Val Lys Leu Pro Gly Ser Lys Ser Leu Ser Asn
             20                  25                  30

Arg Ile Leu Leu Leu Ala Ala Leu Ser Glu Gly Thr Thr Val Val Asp
         35                  40                  45

Asn Leu Leu Asn Ser Glu Asp Val His Tyr Met Leu Gly Ala Leu Arg
     50                  55                  60

Thr Leu Gly Leu Ser Val Glu Ala Asp Lys Ala Ala Lys Arg Ala Val
 65                  70                  75                  80

Val Val Gly Cys Gly Gly Lys Phe Pro Val Glu Asp Ser Ile Glu Glu
```

```
                      85                  90                  95
Val Gln Leu Phe Leu Gly Asn Ala Gly Thr Ala Met Arg Pro Leu Thr
                    100                 105                 110

Ala Ala Val Thr Ala Ala Gly Gly Asn Ala Thr Tyr Val Leu Asp Gly
                    115                 120                 125

Val Pro Arg Met Arg Glu Arg Pro Ile Gly Asp Leu Val Val Gly Leu
            130                 135                 140

Lys Gln Leu Gly Ala Asp Val Asp Cys Phe Leu Gly Thr Asp Cys Pro
145                 150                 155                 160

Pro Val Arg Val Asn Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Asp Lys Leu
            195                 200                 205

Ile Ser Ile Pro Tyr Val Glu Met Thr Leu Arg Leu Met Glu Arg Phe
        210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
        370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
            435                 440                 445

<210> SEQ ID NO 13
<211> LENGTH: 1347
<212> TYPE: DNA
<213> ORGANISM: Artificial Sequence
<220> FEATURE:
<223> OTHER INFORMATION: Encoding Zea mays EPSPS mutant with mutations
      G105(96)A, P110(101)S and K207(194)R

<400> SEQUENCE: 13
```

```
atggcggtgc aggcgggtgc cgaggagatc gtgctgcagc ccatcaagga gatctccggc    60
accgtcaagc tgccggggtc caagtcgctt tccaaccgga tcctcctgct cgccgccctg   120
tccgaggga caacagtggt tgataacctg ttgaacagtg aggatgtcca ctacatgctc    180
ggggccttga ggactcttgg tctctctgtc gaagcggaca agctgccaa aagagctgta   240
gttgttggct gtggtggaaa gttcccagtt gaggattcta agaggaagt gcagctcttc   300
ttggggaatg ctgcgactgc aatgcggtcc ttgacagcag ctgttactgc tgctggtgga   360
aatgcaactt acgtgcttga tggagtacca agaatgaggg agagacccat ggcgacttg    420
gttgtcggat tgaagcagct tggtgcagat gttgattgtt ccttggcac tgactgccca    480
cctgttcgtg tcaatggaat cggagggcta cctggtggca aggtcaagct gtctggctcc   540
atcagcagtc agtacttgag tgccttgctg atggctgctc ctttggctct tggggatgtg   600
gagattgaaa tcattgatag attaatctcc attccctacg tcgaaatgac attgagattg   660
atggagcgtt ttggtgtgaa agcagagcat tctgatagct gggacagatt ctacattaag   720
ggaggtcaaa atacaagtc ccctaaaaat gcctatgttg aaggtgatgc ctcaagcgca    780
agctatttct tggctggtgc tgcaattact ggagggactg tgactgtgga aggttgtggc   840
accaccagtt gcagggtga tgtgaagttt gctgaggtac tggagatgat gggagcgaag    900
gttacatgga ccgagactag cgtaactgtt actggcccac gcggggagcc atttgggagg   960
aaacacctca aggcgattga tgtcaacatg aacaagatgc tgatgtcgc catgactctt   1020
gctgtggttg ccctctttgc cgatggcccg acagccatca gagacgtggc ttcctggaga   1080
gtaaaggaga ccgagaggat ggttgcgatc cggacggagc taaccaagct gggagcatct   1140
gttgaggaag ggccggacta ctgcatcatc acgccgccgg agaagctgaa cgtgacggcg   1200
atcgacacgt acgacgacca caggatggcc atggccttct cccttgccgc ctgtgccgag   1260
gtccccgtga ccatccggga ccctgggtgc acccggaaga ccttccccga ctacttcgat   1320
gtgctgagca ctttcgtcaa gaattaa                                      1347
```

<210> SEQ ID NO 14
<211> LENGTH: 448
<212> TYPE: PRT
<213> ORGANISM: Artificial Sequence
<220> FEATURE:
<223> OTHER INFORMATION: Zea mays EPSPS mutant with mutations G105(96)A, P110(101)S and K207(194)R

<400> SEQUENCE: 14

```
Met Ala Val Gln Ala Gly Ala Glu Glu Ile Val Leu Gln Pro Ile Lys
1               5                   10                  15

Glu Ile Ser Gly Thr Val Lys Leu Pro Gly Ser Lys Ser Leu Ser Asn
            20                  25                  30

Arg Ile Leu Leu Leu Ala Ala Leu Ser Glu Gly Thr Thr Val Val Asp
        35                  40                  45

Asn Leu Leu Asn Ser Glu Asp Val His Tyr Met Leu Gly Ala Leu Arg
    50                  55                  60

Thr Leu Gly Leu Ser Val Glu Ala Asp Lys Ala Ala Lys Arg Ala Val
65                  70                  75                  80

Val Val Gly Cys Gly Gly Lys Phe Pro Val Glu Asp Ser Lys Glu Glu
                85                  90                  95

Val Gln Leu Phe Leu Gly Asn Ala Ala Thr Ala Met Arg Ser Leu Thr
            100                 105                 110

Ala Ala Val Thr Ala Ala Gly Gly Asn Ala Thr Tyr Val Leu Asp Gly
```

```
                  115                 120                 125
Val Pro Arg Met Arg Glu Arg Pro Ile Gly Asp Leu Val Val Gly Leu
            130                 135                 140

Lys Gln Leu Gly Ala Asp Val Asp Cys Phe Leu Gly Thr Asp Cys Pro
145                 150                 155                 160

Pro Val Arg Val Asn Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Ile Asp Arg Leu
        195                 200                 205

Ile Ser Ile Pro Tyr Val Glu Met Thr Leu Arg Leu Met Glu Arg Phe
    210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
    290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
    370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
                405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
        435                 440                 445

<210> SEQ ID NO 15
<211> LENGTH: 1347
<212> TYPE: DNA
<213> ORGANISM: Artificial Sequence
<220> FEATURE:
<223> OTHER INFORMATION: Encoding Zea mays EPSPS mutant with mutations
      K94(85)I, G105(96)A, P110(101)S and K207(194)R

<400> SEQUENCE: 15
atggcggtgc aggcgggtgc cgaggagatc gtgctgcagc ccatcaagga gatctccggc      60
accgtcaagc tgccggggtc caagtcgctt ccaaccggga tcctcctgct cgccgccctg     120
tccgagggga caacagtggt tgataacctg ttgaacagtg aggatgtcca ctacatgctc     180
```

```
ggggccttga ggactcttgg tctctctgtc gaagcggaca agctgccaa aagagctgta      240 gttgttggct gtggtggaaa gttcccagtt gaggattcta tagaggaagt gcagctcttc    300
ttggggaatg ctgcgactgc aatgcggtcc ttgacagcag ctgttactgc tgctggtgga    360
aatgcaactt acgtgcttga tggagtacca agaatgaggg agagacccat ggcgacttg     420 gttgtcggat tgaagcagct tggtgcagat gttgattgtt ccttggcac tgactgccca     480 cctgttcgtg tcaatggaat cggagggcta cctggtggca aggtcaagct gtctggctcc    540
atcagcagtc agtacttgag tgccttgctg atggctgctc ctttggctct tggggatgtg    600
gagattgaaa tcattgatag attaatctcc attccctacg tcgaaatgac attgagattg    660
atggagcgtt ttggtgtgaa agcagagcat tctgatagct gggacagatt ctacattaag    720
ggaggtcaaa atacaagtc cctaaaaat gcctatgttg aaggtgatgc ctcaagcgca      780
agctatttct tggctggtgc tgcaattact ggagggactg tgactgtgga aggttgtggc    840
accaccagtt tgcagggtga tgtgaagttt gctgaggtac tggagatgat gggagcgaag    900
gttacatgga ccgagactag cgtaactgtt actggcccac cgcgggagcc atttggagg     960 aaacacctca aggcgattga tgtcaacatg aacaagatgc tgatgtcgc catgactctt     1020 gctgtggttg ccctctttgc cgatggcccg acagccatca gagacgtggc ttcctggaga   1080
gtaaaggaga ccgagaggat ggttgcgatc cggacggagc taaccaagct gggagcatct    1140
gttgaggaag ggccggacta ctgcatcatc acgccgccgg agaagctgaa cgtgacggcg    1200
atcgacacgt acgacgacca caggatggcc atggccttct cccttgccgc ctgtgccgag    1260
gtccccgtga ccatccggga ccctgggtgc acccggaaga ccttccccga ctacttcgat    1320
gtgctgagca ctttcgtcaa gaattaa                                        1347
```

<210> SEQ ID NO 16
<211> LENGTH: 448
<212> TYPE: PRT
<213> ORGANISM: Artificial Sequence
<220> FEATURE:
<223> OTHER INFORMATION: Zea mays EPSPS mutant with mutations K94(85)I,
     G105(96)A, P110(101)S and K207(194)R

<400> SEQUENCE: 16

```
Met Ala Val Gln Ala Gly Ala Glu Glu Ile Val Leu Gln Pro Ile Lys
1               5                   10                  15

Glu Ile Ser Gly Thr Val Lys Leu Pro Gly Ser Lys Ser Leu Ser Asn
            20                  25                  30

Arg Ile Leu Leu Leu Ala Ala Leu Ser Glu Gly Thr Thr Val Val Asp
        35                  40                  45

Asn Leu Leu Asn Ser Glu Asp Val His Tyr Met Leu Gly Ala Leu Arg
    50                  55                  60

Thr Leu Gly Leu Ser Val Glu Ala Asp Lys Ala Ala Lys Arg Ala Val
65                  70                  75                  80

Val Val Gly Cys Gly Gly Lys Phe Pro Val Glu Asp Ser Ile Glu Glu
                85                  90                  95

Val Gln Leu Phe Leu Gly Asn Ala Ala Thr Ala Met Arg Ser Leu Thr
            100                 105                 110

Ala Ala Val Thr Ala Ala Gly Gly Asn Ala Thr Tyr Val Leu Asp Gly
        115                 120                 125

Val Pro Arg Met Arg Glu Arg Pro Ile Gly Asp Leu Val Val Gly Leu
    130                 135                 140

Lys Gln Leu Gly Ala Asp Val Asp Cys Phe Leu Gly Thr Asp Cys Pro
```

```
145                 150                 155                 160
Pro Val Arg Val Asn Gly Ile Gly Gly Leu Pro Gly Gly Lys Val Lys
            165                 170                 175

Leu Ser Gly Ser Ile Ser Ser Gln Tyr Leu Ser Ala Leu Leu Met Ala
        180                 185                 190

Ala Pro Leu Ala Leu Gly Asp Val Glu Ile Glu Ile Asp Arg Leu
    195                 200                 205

Ile Ser Ile Pro Tyr Val Glu Met Thr Leu Arg Leu Met Glu Arg Phe
210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Lys Asn Ala Tyr Val Glu Gly Asp
            245                 250                 255

Ala Ser Ser Ala Ser Tyr Phe Leu Ala Gly Ala Ala Ile Thr Gly Gly
            260                 265                 270

Thr Val Thr Val Glu Gly Cys Gly Thr Thr Ser Leu Gln Gly Asp Val
        275                 280                 285

Lys Phe Ala Glu Val Leu Glu Met Met Gly Ala Lys Val Thr Trp Thr
290                 295                 300

Glu Thr Ser Val Thr Val Thr Gly Pro Pro Arg Glu Pro Phe Gly Arg
305                 310                 315                 320

Lys His Leu Lys Ala Ile Asp Val Asn Met Asn Lys Met Pro Asp Val
            325                 330                 335

Ala Met Thr Leu Ala Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
        370                 375                 380

Pro Asp Tyr Cys Ile Ile Thr Pro Pro Glu Lys Leu Asn Val Thr Ala
385                 390                 395                 400

Ile Asp Thr Tyr Asp Asp His Arg Met Ala Met Ala Phe Ser Leu Ala
            405                 410                 415

Ala Cys Ala Glu Val Pro Val Thr Ile Arg Asp Pro Gly Cys Thr Arg
            420                 425                 430

Lys Thr Phe Pro Asp Tyr Phe Asp Val Leu Ser Thr Phe Val Lys Asn
            435                 440                 445

<210> SEQ ID NO 17
<211> LENGTH: 1359
<212> TYPE: DNA
<213> ORGANISM: Glycine max

<400> SEQUENCE: 17
atggccgccg cagagaagcc ttcgacggcg ccggagatcg tgttggaacc tatcaaagac    60
atctcgggta ccatcacatt gccagggtct aagtctctgt ccaatcgaat tttgcttctt   120
gctgctctct ctgagggaac aactgttgta gacaacttgc tgtacagcga ggatattcat   180
tacatgcttg gtgcattaag gacccttgga ctgcgtgtgg aagacgacca aacaaccaaa   240
caagcaattg tggaaggctg tgggggattg tttcccacta ttaaagaatc taaagatgaa   300
atcaatttat tccttggaaa tgctggtact gcgatgcgtc ctttgacagc agctgtagtt   360
gctgcaggtg aaatgcaag ctacgtactt gatgagtgc cccgaatgag agagaggcca    420 attgggggatt tggttgctgg tcttaagcag ctcggtgcag atgttgattg ctttcttggc   480
```

```
acaaactgtc cacctgttcg tgtaaatggg aagggaggac ttcctggcgg aaaggtgaaa    540
ctgtctggat cagttagcag tcaataccta actgctttgc ttatggcagc tcctttagct    600
cttggcgatg tggaaattga gattgttgat aaactgattt ctgttccata tgttgaaatg    660
actctgaagt tgatggagcg ttttggagtt tctgtggaac acagtggtga ttgggataag    720
ttcttggtcc atggaggtca aaagtacaag tctcctggca atgcttttgt tgaaggtgat    780
gcttcaagtg ccagttactt cctagctggt gcagcagtta ctggtgggac tatcactgtt    840
aatggctgtg gcacaagcag tttacaggga gatgtaaaat ttgctgaagt tcttgaaaag    900
atgggagcta aggttacatg gtcagagaac agtgtcaccg ttactggacc gccacaagat    960
tcttctggtc aaaaagtctt gcaaggcatt gatgtcaata tgaacaagat gccagatgtt   1020
gccatgactc ttgccgttgt cgcactattt gctaatggtc aaactaccat cagagatgtg   1080
gcaagttgga gagttaaaga gactgagagg atgatagcaa tctgcacaga actcagaaag   1140
ctaggagcaa cagttgaaga aggtcctgat tactgtgtga ttactccacc tgagaaattg   1200
aatgtcacag ctatagacac atatgatgac cacagaatgg ccatggcatt ctctcttgct   1260
gcttgtgggg atgttccagt aaccatcaag gatcctggtt gcaccaggaa gacatttccc   1320
gactactttg aagtccttga gaggttcaca aggcactaa                         1359
```

<210> SEQ ID NO 18
<211> LENGTH: 452
<212> TYPE: PRT
<213> ORGANISM: Glycine max

<400> SEQUENCE: 18

Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
                20                  25                  30

Leu Ser Asn Arg Ile Leu Leu Ala Ala Leu Ser Glu Gly Thr Thr
            35                  40                  45

Val Val Asp Asn Leu Leu Tyr Ser Glu Asp Ile His Tyr Met Leu Gly
        50                  55                  60

Ala Leu Arg Thr Leu Gly Leu Arg Val Glu Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
                100                 105                 110

Arg Pro Leu Thr Ala Ala Val Ala Ala Gly Gly Asn Ala Ser Tyr
            115                 120                 125

Val Leu Asp Gly Val Pro Arg Met Arg Glu Arg Pro Ile Gly Asp Leu
        130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Leu Pro Gly
                165                 170                 175

Gly Lys Val Lys Leu Ser Gly Ser Val Ser Ser Gln Tyr Leu Thr Ala
                180                 185                 190

Leu Leu Met Ala Ala Pro Leu Ala Leu Gly Asp Val Glu Ile Glu Ile
            195                 200                 205

Val Asp Lys Leu Ile Ser Val Pro Tyr Val Glu Met Thr Leu Lys Leu

```
                    210                 215                 220
Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
                260                 265                 270

Val Thr Gly Gly Thr Ile Thr Val Asn Gly Cys Gly Thr Ser Ser Leu
                275                 280                 285

Gln Gly Asp Val Lys Phe Ala Glu Val Leu Glu Lys Met Gly Ala Lys
                290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335

Met Pro Asp Val Ala Met Thr Leu Ala Val Val Ala Leu Phe Ala Asn
                340                 345                 350

Gly Gln Thr Thr Ile Arg Asp Val Ala Ser Trp Arg Val Lys Glu Thr
                355                 360                 365

Glu Arg Met Ile Ala Ile Cys Thr Glu Leu Arg Lys Leu Gly Ala Thr
370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
                420                 425                 430

Gly Cys Thr Arg Lys Thr Phe Pro Asp Tyr Phe Glu Val Leu Glu Arg
                435                 440                 445

Phe Thr Arg His
    450

<210> SEQ ID NO 19
<211> LENGTH: 1359
<212> TYPE: DNA
<213> ORGANISM: Artificial Sequence
<220> FEATURE:
<223> OTHER INFORMATION: Encoding Glycine max EPSPS mutant with mutation
      K98(85)T

<400> SEQUENCE: 19
atggccgccg cagagaagcc ttcgacggcg ccggagatcg tgttggaacc tatcaaagac        60
atctcgggta ccatcacatt gccagggtct aagtctctgt ccaatcgaat tttgcttctt       120
gctgctctct ctgagggaac aactgttgta gacaacttgc tgtacagcga ggatattcat       180
tacatgcttg gtgcattaag gacccttgga ctgcgtgtgg aagacgacca aacaaccaaa       240
caagcaattg tggaaggctg tgggggattg tttcccacta ttaaagaatc tacagatgaa       300
atcaatttat ccttggaaaa tgctggtact gcgatgcgtc ctttgacagc agctgtagtt       360
gctgcaggtg gaaatgcaag ctacgtactt gatggagtgc cccgaatgag agagaggcca       420
attggggatt tggttgctgg tcttaagcag ctcggtgcag atgttgattg ctttcttggc       480
acaaactgtc cacctgttcg tgtaaatggg aagggaggac ttcctggcgg aaaggtgaaa       540
ctgtctggat cagttagcag tcaataccta actgctttgc ttatggcagc tccttttagct      600 cttggcgatg tggaaattga gattgttgat aaactgattt ctgttccata tgttgaaatg       660
```

```
actctgaagt tgatggagcg ttttggagtt tctgtggaac acagtggtga ttgggataag    720
ttcttggtcc atggaggtca aaagtacaag tctcctggca atgcttttgt tgaaggtgat    780
gcttcaagtg ccagttactt cctagctggt gcagcagtta ctggtgggac tatcactgtt    840
aatggctgtg gcacaagcag tttacaggga gatgtaaaat ttgctgaagt tcttgaaaag    900
atgggagcta aggttacatg gtcagagaac agtgtcaccg ttactggacc gccacaagat    960
tcttctggtc aaaaagtctt gcaaggcatt gatgtcaata tgaacaagat gccagatgtt   1020
gccatgactc ttgccgttgt cgcactattt gctaatggtc aaactaccat cagagatgtg   1080
gcaagttgga gagttaaaga actgagagg atgatagcaa tctgcacaga actcagaaag   1140
ctaggagcaa cagttgaaga aggtcctgat tactgtgtga ttactccacc tgagaaattg   1200
aatgtcacag ctatagacac atatgatgac cacagaatgg ccatggcatt ctctcttgct   1260
gcttgtgggg atgttccagt aaccatcaag gatcctggtt gcaccaggaa gacatttccc   1320
gactactttg aagtccttga gaggttcaca aggcactaa                          1359
```

<210> SEQ ID NO 20
<211> LENGTH: 452
<212> TYPE: PRT
<213> ORGANISM: Artificial Sequence
<220> FEATURE:
<223> OTHER INFORMATION: Glycine max EPSPS mutant with mutation K98(85)T

<400> SEQUENCE: 20

```
Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
                20                  25                  30

Leu Ser Asn Arg Ile Leu Leu Ala Ala Leu Ser Glu Gly Thr Thr
            35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Thr Asp Glu Ile Asn Leu Phe Leu Gly Asn Ala Gly Thr Ala Met
                100                 105                 110

Arg Pro Leu Thr Ala Ala Val Val Ala Ala Gly Gly Asn Ala Ser Tyr
            115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Leu Pro Gly
                165                 170                 175

Gly Lys Val Lys Leu Ser Gly Ser Val Ser Ser Gln Tyr Leu Thr Ala
                180                 185                 190

Leu Leu Met Ala Ala Pro Leu Ala Leu Gly Asp Val Glu Ile Glu Ile
            195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240
```

Phe Leu Val His Gly Gly Gln Lys Tyr Lys Ser Pro Gly Asn Ala Phe
            245                 250                 255

Val Glu Gly Asp Ala Ser Ser Ala Ser Tyr Phe Leu Ala Gly Ala Ala
        260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
        290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
            325                 330                 335

Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
            355                 360                 365

Glu Arg Met Ile Ala Ile Cys Thr Glu Leu Arg Lys Leu Gly Ala Thr
        370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
            435                 440                 445

Phe Thr Arg His
    450

<210> SEQ ID NO 21
<211> LENGTH: 1359
<212> TYPE: DNA
<213> ORGANISM: Artificial Sequence
<220> FEATURE:
<223> OTHER INFORMATION: Encoding Glycine max EPSPS mutant with mutation
      P114(101)S

<400> SEQUENCE: 21
atggccgccg cagagaagcc ttcgacggcg ccggagatcg tgttggaacc tatcaaagac     60
atctcgggta ccatcacatt gccagggtct aagtctctgt ccaatcgaat tttgcttctt    120
gctgctctct ctgagggaac aactgttgta gacaacttgc tgtacagcga ggatattcat    180
tacatgcttg gtgcattaag gacccttgga ctgcgtgtgg aagacgacca aacaaccaaa    240
caagcaattg tggaaggctg tgggggattg tttcccacta ttaaagaatc taaagatgaa    300
atcaatttat tccttggaaa tgctggtact gcgatgcgta gcttgacagc agctgtagtt    360
gctgcaggtg gaaatgcaag ctacgtactt gatggagtgc cccgaatgag agagaggcca    420
attggggatt tggttgctgg tcttaagcag ctcggtgcag atgttgattg ctttcttggc    480
acaaactgtc cacctgttcg tgtaaatggg aagggaggac ttcctggcgg aaaggtgaaa    540
ctgtctggat cagttagcag tcaataccta actgctttgc ttatggcagc tcctttagct    600
cttggcgatg tggaaattga gattgttgat aaactgattt ctgttccata tgttgaaatg    660
actctgaagt tgatggagcg ttttggagtt tctgtggaac acagtggtga ttgggataag    720 ttccttggtcc atggaggtca aaagtacaag tctcctggca atgcttttgt tgaaggtgat    780

```
gcttcaagtg ccagttactt cctagctggt gcagcagtta ctggtgggac tatcactgtt      840
aatggctgtg gcacaagcag tttacaggga gatgtaaaat ttgctgaagt tcttgaaaag      900
atgggagcta aggttacatg gtcagagaac agtgtcaccg ttactggacc gccacaagat      960
tcttctggtc aaaaagtctt gcaaggcatt gatgtcaata tgaacaagat gccagatgtt     1020
gccatgactc ttgccgttgt cgcactattt gctaatggtc aaactaccat cagagatgtg     1080
gcaagttgga gagttaaaga gactgagagg atgatagcaa tctgcacaga actcagaaag     1140
ctaggagcaa cagttgaaga aggtcctgat tactgtgtga ttactccacc tgagaaattg     1200
aatgtcacag ctatagacac atatgatgac cacagaatgg ccatggcatt ctctcttgct     1260
gcttgtgggg atgttccagt aaccatcaag gatcctggtt gcaccaggaa gacatttccc     1320
gactactttg aagtccttga gaggttcaca aggcactaa                            1359
```

<210> SEQ ID NO 22
<211> LENGTH: 452
<212> TYPE: PRT
<213> ORGANISM: Artificial Sequence
<220> FEATURE:
<223> OTHER INFORMATION: Glycine max EPSPS mutant with mutation
      P114(101)S

<400> SEQUENCE: 22

```
Met Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
                20                  25                  30

Leu Ser Asn Arg Ile Leu Leu Leu Ala Ala Leu Ser Glu Gly Thr Thr
            35                  40                  45

Val Val Asp Asn Leu Leu Tyr Ser Glu Asp Ile His Tyr Met Leu Gly
        50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Ser Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255
```

Val Glu Gly Asp Ala Ser Ser Ala Ser Tyr Phe Leu Ala Gly Ala Ala
              260                 265                 270

Val Thr Gly Thr Ile Thr Val Asn Gly Cys Gly Thr Ser Ser Leu
          275                 280                 285

Gln Gly Asp Val Lys Phe Ala Glu Val Leu Glu Lys Met Gly Ala Lys
        290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
              325                 330                 335

Met Pro Asp Val Ala Met Thr Leu Ala Val Val Ala Leu Phe Ala Asn
        340                 345                 350

Gly Gln Thr Thr Ile Arg Asp Val Ala Ser Trp Arg Val Lys Glu Thr
              355                 360                 365

Glu Arg Met Ile Ala Ile Cys Thr Glu Leu Arg Lys Leu Gly Ala Thr
        370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp His Arg Met Ala Met Ala
              405                 410                 415

Phe Ser Leu Ala Ala Cys Gly Asp Val Pro Val Thr Ile Lys Asp Pro
        420                 425                 430

Gly Cys Thr Arg Lys Thr Phe Pro Asp Tyr Phe Glu Val Leu Glu Arg
              435                 440                 445

Phe Thr Arg His
    450

<210> SEQ ID NO 23
<211> LENGTH: 1359
<212> TYPE: DNA
<213> ORGANISM: Artificial Sequence
<220> FEATURE:
<223> OTHER INFORMATION: Encoding Glycine max EPSPS mutant with
      mutations K98(85)T and P114(101)S

<400> SEQUENCE: 23
atggccgccg cagagaagcc ttcgacggcg ccggagatcg tgttggaacc tatcaaagac      60
atctcgggta ccatcacatt gccagggtct aagtctctgt ccaatcgaat tttgcttctt     120
gctgctctct ctgagggaac aactgttgta gacaacttgc tgtacagcga ggatattcat     180
tacatgcttg gtgcattaag gacccttgga ctgcgtgtgg aagacgacca aacaaccaaa     240
caagcaattg tggaaggctg tggggattg tttcccacta ttaaagaatc tacagatgaa      300
atcaatttat tccttggaaa tgctggtact gcgatgcgta gcttgacagc agctgtagtt     360
gctgcaggtg gaaatgcaag ctacgtactt gatggagtgc ccgaatgag agagaggcca      420 attgggatt tggttgctgg tcttaagcag ctcggtgcag atgttgattg ctttcttggc      480
acaaactgtc cacctgttcg tgtaaatggg aagggaggac ttcctggcgg aaaggtgaaa     540
ctgtctggat cagttagcag tcaataccta actgctttgc ttatggcagc tcctttagct     600
cttggcgatg tggaaattga gattgttgat aaactgattt ctgttccata tgttgaaatg     660
actctgaagt tgatggagcg ttttggagtt tctgtggaac acagtggtga ttgggataag     720
ttcttggtcc atgagggtca aaagtacaag tctcctggca atgcttttgt tgaaggtgat     780
gcttcaagtg ccagttactt cctagctggt gcagcagtta ctggtgggac tatcactgtt     840

```
aatggctgtg gcacaagcag tttacaggga gatgtaaaat ttgctgaagt tcttgaaaag    900
atgggagcta aggttacatg gtcagagaac agtgtcaccg ttactggacc gccacaagat    960
tcttctggtc aaaaagtctt gcaaggcatt gatgtcaata tgaacaagat gccagatgtt   1020
gccatgactc ttgccgttgt cgcactattt gctaatggtc aaactaccat cagagatgtg   1080
gcaagttgga gagttaaaga gactgagagg atgatagcaa tctgcacaga actcagaaag   1140
ctaggagcaa cagttgaaga aggtcctgat tactgtgtga ttactccacc tgagaaattg   1200
aatgtcacag ctatagacac atatgatgac cacagaatgg ccatggcatt ctctcttgct   1260
gcttgtgggg atgttccagt aaccatcaag gatcctggtt gcaccaggaa gacatttccc   1320
gactactttg aagtccttga gaggttcaca aggcactaa                           1359
```

<210> SEQ ID NO 24
<211> LENGTH: 452
<212> TYPE: PRT
<213> ORGANISM: Artificial Sequence
<220> FEATURE:
<223> OTHER INFORMATION: Glycine max EPSPS mutant with mutations
      K98(85)T and P114(101)S

<400> SEQUENCE: 24

```
Met Ala Ala Ala Glu Lys Pro Ser Thr Ala Pro Glu Ile Val Leu Glu
1               5                  10                  15

Pro Ile Lys Asp Ile Ser Gly Thr Ile Thr Leu Pro Gly Ser Lys Ser
                20                  25                  30

Leu Ser Asn Arg Ile Leu Leu Leu Ala Ala Leu Ser Glu Gly Thr Thr
            35                  40                  45

Val Val Asp Asn Leu Leu Tyr Ser Glu Asp Ile His Tyr Met Leu Gly
        50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Thr Asp Glu Ile Asn Leu Phe Leu Gly Asn Ala Gly Thr Ala Met
            100                 105                 110

Arg Ser Leu Thr Ala Ala Val Ala Ala Gly Gly Asn Ala Ser Tyr
            115                 120                 125

Val Leu Asp Gly Val Pro Arg Met Arg Glu Arg Pro Ile Gly Asp Leu
        130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
            260                 265                 270
```

Val Thr Gly Gly Thr Ile Thr Val Asn Gly Cys Gly Thr Ser Ser Leu
            275                 280                 285

Gln Gly Asp Val Lys Phe Ala Glu Val Leu Glu Lys Met Gly Ala Lys
        290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335

Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450

<210> SEQ ID NO 25
<211> LENGTH: 427
<212> TYPE: PRT
<213> ORGANISM: Escherichia coli

<400> SEQUENCE: 25

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys

```
            180                 185                 190
Gly Asp Leu Val Ser Lys Pro Tyr Ile Asp Ile Thr Leu Asn Leu Met
            195                 200                 205

Lys Thr Phe Gly Val Glu Ile Glu Asn Gln His Tyr Gln Gln Phe Val
        210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
        290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Gly His Asp Tyr Ile Arg Ile
        355                 360                 365

Thr Pro Pro Glu Lys Leu Asn Phe Ala Glu Ile Ala Thr Tyr Asn Asp
        370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ggtggctcct acaaatgcca tc                                          22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
gagccaatta acgtcatccc ac                                          22

<210> SEQ ID NO 28
<211> LENGTH: 25
<212> TYPE: DNA
<213> ORGANISM: Artificial Sequence
<220> FEATURE:
<223> OTHER INFORMATION: Primer
```

<400> SEQUENCE: 28
gcttctgacc agcccattat tctgc                                    25

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
ccctcaaggg taagctcatc tctcttc                                  27

<210> SEQ ID NO 30
<211> LENGTH: 51
<212> TYPE: PRT
<213> ORGANISM: Escherichia coli

<400> SEQUENCE: 30

Asn Ala Leu Thr Ala Leu Gly Val Ser Tyr Thr Leu Ser Ala Asp Arg
1               5                   10                  15

Thr Arg Cys Glu Ile Ile Gly Asn Gly Gly Pro Leu His Ala Glu Gly
            20                  25                  30

Ala Leu Glu Leu Phe Leu Gly Asn Ala Gly Thr Ala Met Arg Pro Leu
        35                  40                  45

Ala Ala Ala
    50

<210> SEQ ID NO 31
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ala Leu Lys Ala Leu Gly Leu Ser Val Glu Ala Asp Lys Val Ala
1               5                   10                  15

Lys Arg Ala Val Val Val Gly Cys Gly Gly Lys Phe Pro Val Glu Lys
            20                  25                  30

Asp Ala Ile Glu Glu Val Gln Leu Phe Leu Gly Asn Ala Ala Thr Ala
        35                  40                  45

Met Arg Ser Leu Thr Ala Ala
    50                  55

<210> SEQ ID NO 32
<211> LENGTH: 55
<212> TYPE: PRT
<213> ORGANISM: Oryza sativa

<400> SEQUENCE: 32

Glu Ala Leu Lys Ala Leu Gly Leu Ser Val Glu Ala Asp Lys Val Ala
1               5                   10                  15

Lys Arg Ala Val Val Val Gly Cys Gly Gly Lys Phe Pro Val Glu Lys
            20                  25                  30

Asp Ala Lys Glu Glu Val Gln Leu Phe Leu Gly Asn Ala Gly Thr Ala
        35                  40                  45

Met Arg Pro Leu Thr Ala Ala
    50                  55

<210> SEQ ID NO 33
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Ala Leu Arg Thr Leu Gly Leu Arg Val Glu Asp Asp Gln Thr Thr
1               5                   10                  15

Lys Gln Ala Ile Val Glu Gly Cys Gly Gly Leu Phe Pro Thr Ile Lys
            20                  25                  30

Glu Ser Thr Asp Glu Ile Asn Leu Phe Leu Gly Asn Ala Gly Thr Ala
        35                  40                  45

Met Arg Ser Leu Thr Ala Ala
    50                  55

<210> SEQ ID NO 34
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Ala Leu Arg Thr Leu Gly Leu Ser Val Glu Ala Asp Lys Ala Ala
1               5                   10                  15

Lys Arg Ala Val Val Gly Cys Gly Gly Lys Phe Pro Val Glu Asp
            20                  25                  30

Ser Ile Glu Glu Val Gln Leu Phe Leu Gly Asn Ala Ala Thr Ala Met
        35                  40                  45

Arg Ser Leu Thr Ala Ala
    50

<210> SEQ ID NO 35
<211> LENGTH: 54
<212> TYPE: PRT
<213> ORGANISM: Zea mays

<400> SEQUENCE: 35

Gly Ala Leu Arg Thr Leu Gly Leu Ser Val Glu Ala Asp Lys Ala Ala
1               5                   10                  15

Lys Arg Ala Val Val Gly Cys Gly Gly Lys Phe Pro Val Glu Asp
            20                  25                  30

Ser Lys Glu Glu Val Gln Leu Phe Leu Gly Asn Ala Gly Thr Ala Met
        35                  40                  45

Arg Pro Leu Thr Ala Ala
    50

<210> SEQ ID NO 36
<211> LENGTH: 54
<212> TYPE: PRT
<213> ORGANISM: Escherichia coli

<400> SEQUENCE: 36

Val Ser Ser Gln Phe Leu Thr Ala Leu Leu Met Thr Ala Pro Leu Ala
1               5                   10                  15

Pro Glu Asp Thr Val Ile Arg Ile Lys Gly Asp Leu Val Ser Lys Pro
            20                  25                  30

```
Tyr Ile Asp Ile Thr Leu Asn Leu Met Lys Thr Phe Gly Val Glu Ile
            35                  40                  45

Glu Asn Gln His Tyr Gln
    50

<210> SEQ ID NO 37
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ile Ser Ser Gln Tyr Leu Ser Ala Leu Leu Met Ala Ala Pro Leu Ala
1               5                   10                  15

Leu Gly Asp Val Glu Ile Glu Ile Ile Asp Arg Leu Ile Ser Ile Pro
            20                  25                  30

Tyr Val Glu Met Thr Leu Arg Leu Met Glu Arg Phe Gly Val Lys Ala
            35                  40                  45

Glu His Ser Asp Ser Trp Asp
    50                  55

<210> SEQ ID NO 38
<211> LENGTH: 55
<212> TYPE: PRT
<213> ORGANISM: Zea mays

<400> SEQUENCE: 38

Ile Ser Ser Gln Tyr Leu Ser Ala Leu Leu Met Ala Ala Pro Leu Ala
1               5                   10                  15

Leu Gly Asp Val Glu Ile Glu Ile Ile Asp Lys Leu Ile Ser Ile Pro
            20                  25                  30

Tyr Val Glu Met Thr Leu Arg Leu Met Glu Arg Phe Gly Val Lys Ala
            35                  40                  45

Glu His Ser Asp Ser Trp Asp
    50                  55

<210> SEQ ID NO 39
<211> LENGTH: 55
<212> TYPE: PRT
<213> ORGANISM: Glycine max

<400> SEQUENCE: 39

Gly Ala Leu Arg Thr Leu Gly Leu Arg Val Glu Asp Asp Gln Thr Thr
1               5                   10                  15

Lys Gln Ala Ile Val Glu Gly Cys Gly Gly Leu Phe Pro Thr Ile Lys
            20                  25                  30

Glu Ser Lys Asp Glu Ile Asn Leu Phe Leu Gly Asn Ala Gly Thr Ala
            35                  40                  45

Met Arg Pro Leu Thr Ala Ala
    50                  55
```

K85 MUTATION-CONTAINING PLANT EPSPS MUTANT, AND ENCODING GENE AND APPLICATION THEREOF

CROSS-REFERENCE TO RELATED APPLICATIONS

This application is a national stage application of PCT/CN2018/121331 filed on Dec. 14, 2018, the disclosure of which is incorporated herein by reference in entirety. The present disclosure claims the priorities to the Chinese patent application with the filing number 201711062251.2 filed on Nov. 2, 2017 with the Chinese Patent Office and entitled "K85 Mutation-containing Plant EPSPS Mutant, and Encoding Gene and Application thereof" and the Chinese patent application with the filing number 201811070065.8 filed on Sep. 13, 2018 with the Chinese Patent Office and entitled "K85 Mutation-containing Plant EPSPS Mutant, and Encoding Gene and Application thereof," which are incorporated herein by reference in entirety.

TECHNICAL FIELD

The present disclosure relates to the technical field of gene engineering, in particular to a K85 mutation-containing plant EPSPS mutant, and an encoding gene and use thereof.

BACKGROUND ART

Glyphosate is one of the most common herbicides currently used in the world, and has been used for nearly 40 years up to now. Glyphosate inhibits activity of 5-enolpyruvylshikimate-3-phosphate synthase (EPSPS). EPSPS catalyzes PEP and shikimate-3-phosphate to synthesize EPSP in a shikimic acid pathway, and finally leads to the synthesis of aromatic amino acid tryptophan, phenylalanine and tyrosine. Glyphosate blocks the synthesis of these aromatic amino acids, thereby affecting normal growth of plants, and eventually causing death of affected plants.

At present, a main method for creating a glyphosate-resistant breed is to use gene engineering to transform a glyphosate-resistant gene derived from bacteria into the crop, thereby cultivating a new breed of transgenic glyphosate-resistant crop. Since the launch beginning in 1996, the cultivated area has increased quickly, and as of 2015, the cultivated area of the glyphosate-resistant transgenic crops in the world has reached 150 million hectares, accounting for 83% of total cultivated area of transgenic crops, and bringing huge benefits to agricultural production and environment.

However, the most widely used glyphosate-resistant gene currently in agriculture is CP4 EPSPS derived from *Agrobacterium tumefaciens* CP4 strain. Although many EPSPS genes capable of resisting glyphosate have been found from microorganisms, these genes have not been widely used in crops. To use glyphosate-resistant genes derived from these microorganisms in crops, these genes, e.g. CP4 EPSPS, are expressed in crops by transgenic methods, resulting in transgenic crops. Although transgenic crops produced thereby have been commercialized at quite large area, public acceptance of transgenic crops is still a major issue around the globe, and even in America with the largest cultivated area of transgenic crops, the transgenic crops are mainly limited to a few crops such as maize, soybean, and cotton.

SUMMARY

An object of the present disclosure is to provide a plant EPSPS mutant (i.e. 5-enolpyruvylshikimate-3-phosphate synthase mutant), which is derived from plant, and has glyphosate resistance after mutation.

Another object of the present disclosure is to provide an encoding gene, which can encode the above plant EPSPS mutant.

Another object of the present disclosure is to provide a vector containing the above encoding gene.

Another object of the present disclosure is to provide a cell containing the above vector.

Another object of the present disclosure is to provide use of the above plant EPSPS mutant.

The present disclosure is achieved as follows:

A plant EPSPS mutant, compared with *E. coli* (*Escherichia coli*) EPSPS, the amino acid sequence of the plant EPSPS mutant contains a mutation corresponding to the site 85 of the *E. coli* EPSPS.

An encoding gene, which encodes the above plant EPSPS mutant.

A vector containing the above encoding gene.

A recombinant cell containing the above vector.

Use of the above plant EPSPS mutant in cultivation of glyphosate-resistant plants.

The Present Disclosure has the Following Beneficial Effects

A plant EPSPS mutant provided in the present disclosure, compared with *E. coli* EPSPS, the amino acid sequence of the plant EPSPS mutant contains a mutation such as mutation to T or I corresponding to the site 85 of the *E. coli* EPSPS. This mutation site corresponds to an amino acid residue at site 100 of rice EPSPS, site 94 of maize EPSPS and site 98 of soybean EPSPS. The mutation of such site significantly improves resistance of various EPSPS mutants of multiple types of plant to glyphosate, and also maintains its own catalytic activity of biological enzyme. A plant or a recombinant bacterium transformed by the plant EPSPS mutant provided in the present disclosure can grow normally in the presence of glyphosate, and the plant EPSPS mutant not only can be used for cultivation of transgenic crop, but also can be used for cultivating glyphosate-resistant non-transgenic plants such as rice, tobacco, soybean, maize, wheat, cotton and sorghum, and has a broad application prospect.

SEQUENCE LISTING

This application includes a sequence listing, which is herein incorporated by reference and was filed electronically as an ASCII text file and entitled "046231_000041_SL.txt" and it was created on Nov. 20, 2020 and is 81,311 bytes in size.

BRIEF DESCRIPTION OF DRAWINGS

In order to more clearly illustrate technical solutions of examples of the present disclosure, drawings which need to be used for the examples will be introduced briefly below, and it should be understood that the drawings below merely show some examples of the present disclosure, therefore, they should not be considered as limitation on the scope, and those ordinarily skilled in the art still could obtain other relevant drawings according to these drawings, without any creative effort.

FIG. 3 is a graph showing growth results of *E. coli* transformed by a gene, which encodes the soybean EPSPS mutant provided in Example 4, in Example 7 of the present disclosure, in culture media containing different glyphosate concentrations;

FIG. 4 is a schematic structural diagram of a pADV5 vector in Example 5 of the present disclosure;

FIG. 5 shows partial alignment results of amino acid sequences of the three, namely, *E. coli* EPSPS (SEQ ID NO: 30)(see first line of the alignment entitled "Ec-EPSPS WT"), rice EPSPS mutant II (SEQ ID NO: 31)(see second line of the alignment entitled "Os-EPSPS M") and wild-type rice EPSPS (SEQ ID NO: 32) (see third line of the alignment entitled "Os-EPSPS WT") in Example 2 of the present disclosure;

FIG. 6 shows partial alignment results of amino acid sequences of the three, namely, *E. coli* EPSPS, the maize EPSPS mutant and the wild-type maize EPSPS in Example 3 of the present disclosure (FIG. discloses SEQ ID NOS 30 and 34-38, respectively, in order of appearance (the portion of Ec-EPSPS WT shown is provided also as SEQ ID NO: 30; the portion of Zm-EPSPS M shown is provided also as SEQ ID NO: 34; the portion of Zm-EPSPS WT shown is provided also as SEQ ID NO: 35; the portion of Ec-EPSPS WT shown is also provided as SEQ ID NO:36; the portion of Zm-EPSPS M shown is also provided as SEQ ID NO:37; the portion of Zm-EPSPS WT shown is provided also as SEQ ID NO: 38.

FIG. 7 shows partial alignment results of amino acid sequences of the three, namely, *E. coli* EPSPS (SEQ ID NO: 30)(see first line of the alignment entitled "Ec-EPSPS WT"), the soybean EPSPS mutant (SEQ ID NO: 33)(see second line of the alignment entitled "Gm-EPSPS M") and wild-type soybean EPSPS (SEQ ID NO: 39)(see third line of the alignment entitled "Gm-EPSPS WT") in Example 4 of the present disclosure; and FIG. 8 is a schematic structural diagram of a pGVP1-EPSPS vector provided in Experiment Example 8 of the present disclosure.

DETAILED DESCRIPTION OF EMBODIMENTS

Figure 1:
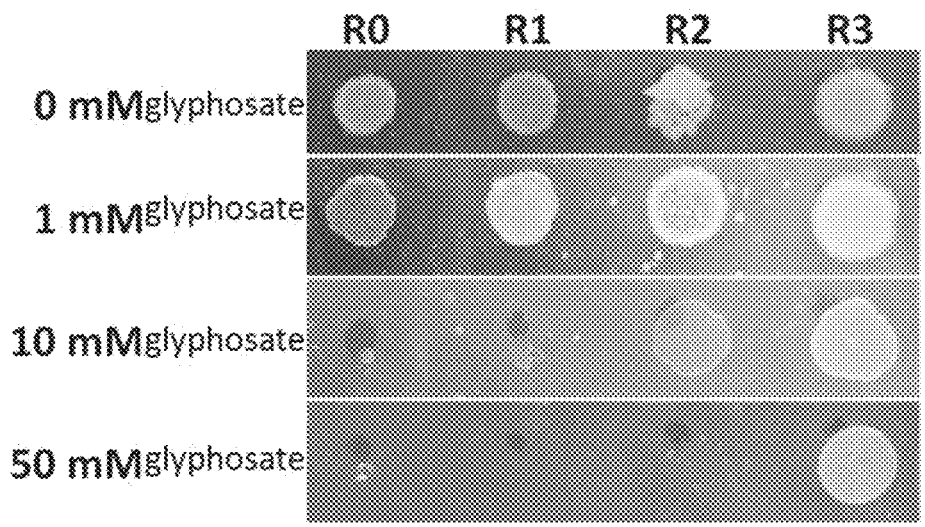
FIG. 1 is a graph showing growth results of *E. coli* transformed by a gene, which encodes the rice EPSPS mutant provided in Example 1 and Example 2, in Example 5 of the present disclosure, in culture media containing different glyphosate concentrations.
Figure 2:
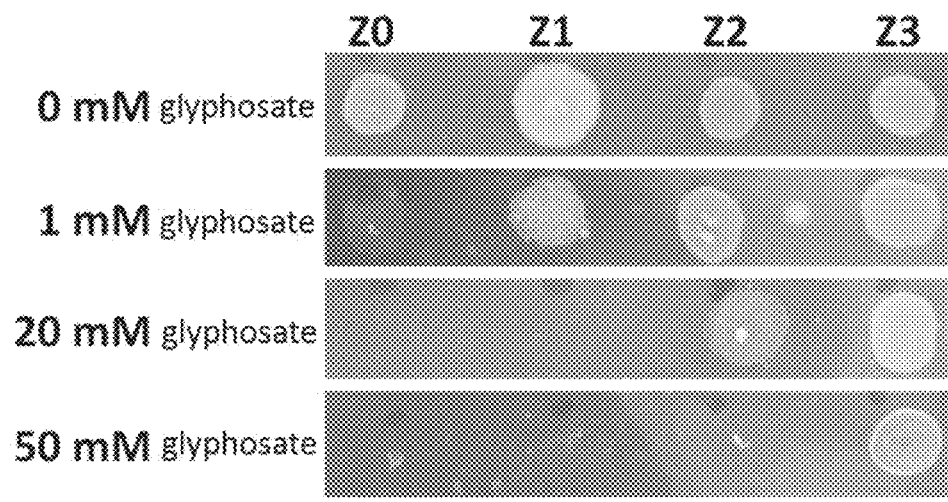
FIG. 2 is a graph showing growth results of *E. coli* transformed by a gene, which encodes the maize EPSPS mutant provided in Example 3, in Example 6 of the present disclosure, in culture media containing different glyphosate concentrations.

In order to make the objects, technical solutions and advantages of the examples of the present disclosure clearer, the technical solutions in the examples of the present disclosure will be described below clearly and completely. If no specific conditions are specified in the examples, they are carried out under normal conditions or conditions recommended by manufacturers. If manufacturers of reagents or apparatuses used are not specified, they are conventional products commercially available.

A plant EPSPS mutant containing mutations K85T and K85I, an encoding gene and use thereof provided in the present disclosure are specifically described below.

In one aspect, the present disclosure provides a plant EPSPS mutant (i.e. 5-enolpyruvylshikimate-3-phosphate synthase mutant), and compared with *E. coli* EPSPS, the amino acid sequence of the plant EPSPS mutant contains a mutation corresponding to the site 85 of the *E. coli* EPSPS.

The mutation of such site can significantly improve glyphosate resistance of the plant EPSPS mutant.

Further, in some embodiments of the present disclosure, the amino acid sequence of the plant EPSPS mutant contains a mutation of K to T or K to I, that is, K to T or K to I, corresponding to the site 85 of the *E. coli* EPSPS.

Or it can be understood as follows: aligning the amino acid sequence of the plant EPSPS mutant with the amino acid sequence of the *E. coli* EPSPS, an amino acid residue of the amino acid sequence of the plant EPSPS mutant corresponding to the site 85 of the *E. coli* EPSPS is mutated from K to T ("K85T" for short) or mutated from K to I ("K85I" for short).

Further, in some embodiments of the present disclosure, the amino acid sequence of the *E. coli* EPSPS is represented by SEQ ID NO: 25.

That is to say, aligning the amino acid sequence of the plant EPSPS mutant with the amino acid sequence of the *E. coli* EPSPS represented by SEQ ID NO: 25, an amino acid residue of the amino acid sequence of the plant EPSPS mutant corresponding to the site 85 represented by SEQ ID NO: 25 is mutated from K to T or mutated from K to I.

Further, in some embodiments of the present disclosure, the amino acid sequence of the plant EPSPS mutant further contains one of the following mutations corresponding to the *E. coli* EPSPS: G96A, P101S and K194R or any combination thereof.

The mutation G96A can be understood as follows: aligning the amino acid sequence of the plant EPSPS mutant with the amino acid sequence of the *E. coli* EPSPS, an amino acid residue of the amino acid sequence of the plant EPSPS mutant corresponding to the site 96 of the *E. coli* EPSPS is mutated from G to A.

The mutation P101S can be understood as follows: aligning the amino acid sequence of the plant EPSPS mutant with the amino acid sequence of the *E. coli* EPSPS, an amino acid residue of the amino acid sequence of the plant EPSPS mutant corresponding to the site 101 of the *E. coli* EPSPS is mutated from P to S.

The mutation K194R can be understood as follows: aligning the amino acid sequence of the plant EPSPS mutant with the amino acid sequence of the *E. coli* EPSPS, an amino acid residue of the amino acid sequence of the plant EPSPS mutant corresponding to the site 194 of the *E. coli* EPSPS is mutated from K to R.

One of G96A, P101S and K194R or a combination of several mutations combined with the mutation at site 85, for example, mutation K85T or K85I can enhance the glyphosate resistance of the plant EPSPS mutant, and can maintain the bio-enzyme activity of the plant EPSPS mutant.

Further, in some embodiments of the present disclosure, the plant EPSPS mutant is derived from, but is not limited to, the following plants: wheat, rice, barley, oat, maize, sorghum, millet, buckwheat, maiden cane, mung bean, broad bean, pea, lentil, sweet potato, potato, cotton, soybean, rape, sesame, peanut, sunflower, radish, carrot, turnip, beet, Chinese cabbage, mustard, cabbage, cauliflower, Chinese kale, cucumber, zucchini, pumpkin, wax gourd, balsam pear, loofah, snake melon, watermelon, melon, tomato, eggplant, pepper, kidney bean, cowpea, green soy bean, Chinese chives, welsh onion, onion, leek, spinach, celery, amaranth, lettuce, crowndaisy *chrysanthemum*, daylily, grape, strawberry, beet, sugarcane, tobacco, alfalfa, pasture grass, turfgrass, tea and cassava.

That is to say, the plant EPSPS mutant provided in the present disclosure is obtained after the above mutation of wild-type EPSPS derived from plants such as rice, tobacco, soybean, maize, wheat, cotton, rape and sorghum, and it maintains the plant source characteristics. An encoding gene encoding this plant EPSPS mutant can be applied to the cultivation of glyphosate-resistant crop varieties, for example, a transgenic or genetic modification method can be adopted to realize the cultivation purpose. Compared with the existing mode of transforming the glyphosate-resistant genes from microorganisms, directly transforming the glyphosate-resistant genes from plant sources or editing the genome with the glyphosate-resistant genes from plant sources as a template has more reliable biological safety, which is favorable for the popularization and the application of new glyphosate-resistant varieties, and improves the public acceptance.

Preferably, in some embodiments of the present disclosure, the plant EPSPS mutant is derived from rice (*Oryza sativa*), and the amino acid sequence of the plant EPSPS mutant is represented by SEQ ID NO: 4. The plant EPSPS mutant represented by SEQ ID NO: 4 is a rice EPSPS mutant I. Compared with the amino acid sequence of the wild-type rice EPSPS represented by SEQ ID NO: 2, the rice EPSPS mutant I contains one mutation K100(85)I.

The K100(85)I mutation can be understood as follows: compared with the wild-type rice EPSPS, an amino acid residue at site 100 in SEQ ID NO: 2 of the rice EPSPS mutant is mutated from K to I, and this site corresponds to site 85 of the *E. coli* EPSPS.

Preferably, in some embodiments of the present disclosure, the plant EPSPS mutant is derived from rice, and the amino acid sequence of the plant EPSPS mutant contains following mutations corresponding to the *E. coli* EPSPS: K85I, G96A and P101S.

Further preferably, in some embodiments of the present disclosure, the amino acid sequence of the plant EPSPS mutant is represented by SEQ ID NO: 8.

The plant EPSPS mutant represented SEQ ID NO: 8 is a rice EPSPS mutant II. Compared with the amino acid sequence of the wild-type rice EPSPS represented by SEQ ID NO: 2, the rice EPSPS mutant II contains three mutations: K100(85)I, G111(96)A and P116(101)S.

The G111(96)A mutation can be understood as follows: compared with the wild-type rice EPSPS, an amino acid residue at site 111 in SEQ ID NO: 2 of the rice EPSPS mutant II is mutated from G to A, and this site corresponds to site 96 of the *E. coli* EPSPS.

The P116(101)S mutation can be understood as follows: compared with the wild-type rice EPSPS, an amino acid residue at site 116 in SEQ ID NO: 2 of the rice EPSPS mutant II is mutated from P to S, and this site corresponds to site 101 of the *E. coli* EPSPS.

Further, in some embodiments of the present disclosure, the plant EPSPS mutant is derived from maize (*Zea mays*), and the amino acid sequence of the plant EPSPS mutant contains following mutations corresponding to the *E. coli* EPSPS: K85I, G96A, P101S and K194R.

Further, in some embodiments of the present disclosure, the amino acid sequence of the plant EPSPS mutant is represented by SEQ ID NO: 16.

The plant EPSPS mutant represented by SEQ ID NO: 16 is a maize EPSPS mutant. Compared with the amino acid sequence of the wild-type maize EPSPS represented by SEQ ID NO: 10, the maize EPSPS mutant contains four mutations: K94(85)I, G105(96)A, P110(101)S and K207(194)R.

The K94(85)I mutation can be understood as follows: compared with the wild-type maize EPSPS, an amino acid residue at site 94 in SEQ ID NO: 10 of the maize EPSPS mutant is mutated from K to I, and this site corresponds to site 85 of the *E. coli* EPSPS.

The G105(96)A mutation can be understood as follows: compared with the wild-type maize EPSPS, an amino acid residue at site 105 in SEQ ID NO: 10 of the maize EPSPS mutant is mutated from G to A, and this site corresponds to site 96 of the *E. coli* EPSPS.

The P110(101)S mutation can be understood as follows: compared with the wild-type maize EPSPS, an amino acid residue at site 110 in SEQ ID NO: 10 of the maize EPSPS mutant is mutated from P to S, and this site corresponds to site 101 of the *E. coli* EPSPS.

The K207(194)R mutation can be understood as follows: compared with the wild-type maize EPSPS, an amino acid residue at site 207 in SEQ ID NO: 10 of the maize EPSPS mutant is mutated from K to R, and this site corresponds to site 194 of the *E. coli* EPSPS.

Further, in some embodiments of the present disclosure, the plant EPSPS mutant is derived from soybean (*Glycine max* (Linn.) Merr.), and the amino acid sequence of the plant EPSPS mutant further contains following mutations corresponding to the *E. coli* EPSPS: K85T and P101S.

Further, in some embodiments of the present disclosure, the amino acid sequence of the plant EPSPS mutant is represented by SEQ ID NO: 24.

The plant EPSPS mutant represented by SEQ ID NO: 24 is a soybean EPSPS mutant. Compared with the amino acid sequence of the wild-type soybean EPSPS represented by SEQ ID NO: 18, the soybean EPSPS mutant contains two mutations: K98(85)T and P114(101)S.

The K98(85)T mutation can be understood as follows: compared with the wild-type soybean EPSPS, an amino acid residue at site 98 in SEQ ID NO: 18 of the soybean EPSPS mutant is mutated from K to T, and this site corresponds to site 85 of the *E. coli* EPSPS.

The P114(101)S mutation can be understood as follows: compared with the wild-type soybean EPSPS, an amino acid residue at site 114 in SEQ ID NO: 18 of the soybean EPSPS mutant is mutated from P to S, and this site corresponds to site 101 of the *E. coli* EPSPS.

In another aspect, the present disclosure provides an encoding gene, which encodes the above plant EPSPS mutant.

According to degeneracy of codon, a nucleotide encoding sequence of the EPSPS mutant can be quite easily obtained on the basis of the amino acid sequence of the above plant EPSPS mutant. The encoding gene will fall within the scope of protection of the present disclosure as long as the above plant EPSPS mutant can be encoded.

Further, in some embodiments of the present disclosure, the above encoding gene is represented by SEQ ID NO: 3, 7, 15 or 23.

SEQ ID NO: 3 shows an encoding gene of the rice EPSPS mutant I, which encodes the rice EPSPS mutant I represented by SEQ ID NO: 4.

The sequence represented by SEQ ID NO: 7 is an encoding gene of the rice EPSPS mutant II, which encodes the rice EPSPS mutant II represented by SEQ ID NO: 8.

The sequence represented by SEQ ID NO: 15 is an encoding gene of the maize EPSPS mutant, which encodes the maize EPSPS mutant represented by SEQ ID NO: 16.

The sequence represented by SEQ ID NO: 23 is an encoding gene of the soybean EPSPS mutant, which encodes the soybean EPSPS mutant represented by SEQ ID NO: 24.

A person skilled in the art, according to degeneracy of codon, could easily substitute one or more nucleotides on the basis of sequences of the above encoding genes, to obtain corresponding derivative sequences, such that the plant EPSPS mutant provided in the present disclosure is encoded. Therefore, substituting one or more nucleotides on the basis of sequences of the above encoding genes to obtain corresponding derivative sequences, encoding the plant EPSPS mutant provided in the present disclosure, also falls into the scope of protection of the present disclosure.

In another aspect, the present disclosure provides a vector containing the above encoding gene.

Further, in some embodiments of the present disclosure, the vector may be a cloning vector or an expression vector, and further, in some embodiments of the present disclosure, the expression vector may be a prokaryotic expression vector, for example, pADV5 vector, or a eukaryotic expression vector. Further, in some embodiments of the present disclosure, the eukaryotic expression vector is a plant expression vector, for example, pBI121 vector.

It is easily understood that a person skilled in the art could select a suitable vector as a tool for carrying the above encoding genes according to needs, which falls into the scope of protection of the present disclosure.

In another aspect, the present disclosure provides a recombinant bacterium or a recombinant cell containing the above vector.

Further, in some embodiments of the present disclosure, the recombinant bacterium may be a coccus, a *bacillus*, for example, *E. coli*, or a *helicobacter*; it also may be an autotrophic bacterium or a heterotrophic bacterium.

Further, in some embodiments of the present disclosure, the recombinant cell may be a prokaryotic cell or a eukaryotic cell; further, in some embodiments of the present disclosure, the eukaryotic cell may be an animal cell, or may be a plant cell; further, in some embodiments of the present disclosure, the plant cell may be a dicotyledonous plant cell or a monocotyledonous plant cell.

It is easily understood that a person skilled in the art could select a suitable bacterium or cell as a host of the above encoding genes according to needs, which falls into the scope of protection of the present disclosure.

In another aspect, the present disclosure provides use of the above plant EPSPS mutant in cultivation of glyphosate-resistant plants.

Further, in some embodiments of the present disclosure, the above use includes: transforming a target plant with a vector, wherein the vector contains an encoding gene that encodes the plant EPSPS mutant.

For example, a complete rice plant is formed by transforming, e.g. rice callus, with a vector containing a gene that encodes the rice EPSPS represented by SEQ ID NO: 7, and culturing to make the transformed rice callus differentiated, then the transgenic glyphosate-resistant rice can be cultivated.

Further, in some embodiments of the present disclosure, the above use includes: modifying an endogenous EPSPS gene of a target plant such that the plant EPSPS mutant is encoded.

For example, a non-transgenic rice can be cultivated by modifying the endogenous EPSPS gene of the rice genome with a part or all of the gene encoding the rice EPSPS represented by SEQ ID NO: 7 as a template.

Further, in some embodiments of the present disclosure, the above use includes: carrying out mutagenesis in a plant cell, tissue, individual or population such that the plant EPSPS mutant is encoded.

For example, mutagenesis, such as chemical mutagenesis and radiation mutagenesis, is carried out to the rice material, with the gene encoding the rice EPSPS represented by SEQ ID NO: 7 as a guide, and then rice with endogenous EPSPS gene mutation can be cultivated. For example, an encoding sequence of the endogenous EPSPS gene further can be modified to a base sequence (SEQ ID NO: 7) of the encoding gene through CRISPR/Cas9 technology, and the same protein as the rice EPSPS mutant (SEQ ID NO: 8) provided in the present disclosure is encoded in the target plant, such that the target plant has glyphosate resistance.

Further, in some embodiments of the present disclosure, the target plant is any one of rice, tobacco, soybean, maize, wheat, cotton, rape, sorghum and other plants.

It is easily understood that a person skilled in the art could select the crop variety required to be cultivated according to the needs, which fall within the scope of protection of the present disclosure as long as the plant EPSPS mutant and/or the encoding gene thereof provided in the present disclosure are/is applied.

It should be indicated that, the alignment method used in the protein sequence alignment involved in the present disclosure is Clustal online alignment, which is available on line. Results obtained using other sequence alignment tools (e.g., DNAMAN, with relevant parameter settings set by default) are substantially identical to that obtained by the Clustal online alignment.

To sum up, compared with the *E. coli* EPSPS, the amino acid sequence of the plant EPSPS mutant provided in the present disclosure contains the mutation such as mutation of K to T or K to I corresponding to the site 85 of the *E. coli* EPSPS. The position of this mutation site corresponds to site 100 of the wild-type rice EPSPS (SEQ ID NO: 2), to site 94 of the wild-type maize EPSPS (SEQ ID NO: 10), and to site 98 of the wild-type soybean EPSPS (SEQ ID NO: 18). The mutation of such site can significantly improve resistance of various EPSPS mutants of multiple types of plant to glyphosate, and meanwhile maintain the catalytic activity of biological enzyme of the mutants themselves. A plant or a recombinant bacterium transformed by the plant EPSPS mutant can grow normally, the plant EPSPS mutant not only can be used for cultivation of transgenic crop, but also can be used for cultivating glyphosate-resistant non-transgenic plants such as rice, tobacco, soybean, maize, wheat, cotton and sorghum, which has a broad application prospect.

The features and performances of the present disclosure are further described in detail below in combination with examples.

Example 1

The present example provides a plant EPSPS mutant, which is derived from rice and is a rice EPSPS mutant I, and it is obtained after mutating a wild-type rice EPSPS (with an amino acid sequence represented by SEQ ID NO: 2), and has an amino acid sequence represented by SEQ ID NO: 4.

Compared with the amino acid sequence of the wild-type rice EPSPS represented by SEQ ID NO: 2, the rice EPSPS mutant I provided in the present example contains one mutation K100(85)I.

That is, compared with the wild-type rice EPSPS, an amino acid residue at site 100 of the rice EPSPS mutant I is mutated from K to I, and this site corresponds to site 85 of the *E. coli* EPSPS.

The present example further provides a rice EPSPS mutant I encoding gene (a gene encoding the rice EPSPS mutant I) that encodes the above rice EPSPS mutant I, of which a nucleotide sequence is represented by SEQ ID NO: 3.

The gene encoding the rice EPSPS mutant I, and the rice EPSPS mutant I provided in the example of the present disclosure both can be obtained through a chemical synthesis method.

Example 2

The present example provides a plant EPSPS mutant, which is derived from rice and is a rice EPSPS mutant II, and it is obtained after mutating a wild-type rice EPSPS (with an amino acid sequence represented by SEQ ID NO: 2), and has an amino acid sequence represented by SEQ ID NO: 8.

Compared with the amino acid sequence of the wild-type rice EPSPS represented by SEQ ID NO: 2, the rice EPSPS mutant II contains three mutations: K100(85)I, G111(96)A and P116(101)S.

That is, as shown in FIG. 5 (FIG. 5 shows partial alignment results of amino acid sequences of the three, namely, *E. coli* EPSPS, rice EPSPS mutant II and wild-type rice EPSPS, wherein Ec-EPSPS WT represents the *E. coli* EPSPS; Os-EPSPS M represents the rice EPSPS mutant II; and Os-EPSPS WT represents the wild-type rice EPSPS), compared with the wild-type rice EPSPS, an amino acid residue at site 100 of the rice EPSPS mutant II is mutated from K to I, and this site corresponds to site 85 of the *E. coli* EPSPS (SEQ ID NO: 25); an amino acid residue at site 111 is mutated from G to A, and this site corresponds to site 96 of the *E. coli* EPSPS; an amino acid residue at site 116 is mutated from P to S, and this site corresponds to site 101 of the *E. coli* EPSPS (e.g. sites indicated by arrows in FIG. 5).

The present example further provides a rice EPSPS mutant II encoding gene (a gene encoding the rice EPSPS mutant II) that encodes the above rice EPSPS mutant II, of which a nucleotide sequence is represented by SEQ ID NO: 7.

The gene encoding the rice EPSPS mutant II, and the rice EPSPS mutant II provided in the example of the present disclosure both can be obtained through a chemical synthesis method.

Example 3

The present example provides a plant EPSPS mutant, which is derived from maize and is a maize EPSPS mutant, and it is obtained after mutating a wild-type maize EPSPS (with an amino acid sequence represented by SEQ ID NO: 10), and has an amino acid sequence represented by SEQ ID NO: 16.

Compared with the amino acid sequence of the wild-type maize EPSPS represented by SEQ ID NO: 10, the maize EPSPS mutant provided in the present example contains four mutations: K94(85)I, G105(96)A, P110(101)S and K207(194)R.

That is, as shown in FIG. 6 (FIG. 6 shows partial alignment results of amino acid sequences of the three, namely, *E. coli* EPSPS, maize EPSPS mutant and wild-type maize EPSPS, wherein Ec-EPSPS WT represents the *E. coli* EPSPS; Zm-EPSPS M represents the maize EPSPS mutant; and Zm-EPSPS WT represents the wild-type maize EPSPS), compared with the wild-type maize EPSPS, an amino acid residue at site 94 of the maize EPSPS mutant is mutated from K to I, and this site corresponds to site 85 of the *E. coli* EPSPS; an amino acid residue at site 105 is mutated from G to A, and this site corresponds to site 96 of the *E. coli* EPSPS; an amino acid residue at site 110 is mutated from P to S, and this site corresponds to site 101 of the *E. coli* EPSPS; and an amino acid residue at site 207 is mutated from K to R, and this site corresponds to site 194 of the *E. coli* EPSPS (e.g. sites indicated by arrows in FIG. 6).

An example of the present disclosure further provides a maize EPSPS mutant encoding gene (a gene encoding the maize EPSPS mutant) that encodes the above maize EPSPS mutant, of which a nucleotide sequence is represented by SEQ ID NO: 15.

The gene encoding the maize EPSPS mutant, and the maize EPSPS mutant provided in the example of the present disclosure both can be obtained through a chemical synthesis method.

Example 4

The present example provides a plant EPSPS mutant, which is derived from soybean and is a soybean EPSPS mutant, and it is obtained after mutating a wild-type soybean EPSPS (with an amino acid sequence represented by SEQ ID NO: 18), and has an amino acid sequence represented by SEQ ID NO: 24.

Compared with the amino acid sequence of the wild-type soybean EPSPS represented by SEQ ID NO: 18, the soybean EPSPS mutant contains two mutations: K98(85)T and P114(101)S.

That is, as shown in FIG. 7 (FIG. 7 shows partial alignment results of amino acid sequences of the three, namely, *E. coli* EPSPS, soybean EPSPS mutant and wild-type soybean EPSPS, wherein Ec-EPSPS WT represents the *E. coli* EPSPS; Gm-EPSPS M represents the soybean EPSPS mutant; and Gm-EPSPS WT represents the wild-type soybean EPSPS), compared with the wild-type soybean EPSPS, an amino acid residue at site 98 of the soybean EPSPS mutant is mutated from K to T, and this site corresponds to site 85 of the *E. coli* EPSPS (SEQ ID NO: 25); and an amino acid residue at site 114 is mutated from P to S, and this site corresponds to site 101 of the *E. coli* EPSPS (e.g. sites indicated by arrows in FIG. 7).

An example of the present disclosure further provides a soybean EPSPS mutant encoding gene (a gene encoding the soybean EPSPS mutant) that encodes the above soybean EPSPS mutant, of which a nucleotide sequence is represented by SEQ ID NO: 23.

The gene encoding the soybean EPSPS mutant, and the soybean EPSPS mutant provided in the example of the present disclosure both can be obtained through a chemical synthesis method.

Example 5

*E. coli* transformed by the gene (SEQ ID NO: 3) encoding the rice EPSPS mutant I provided in Example 1 was taken as Experiment Group 1 (only containing a mutation K100(85)I).

*E. coli* transformed by the gene (with a nucleotide sequence represented by SEQ ID NO: 5, and an amino acid sequence of the encoded rice EPSPS mutant is represented by SEQ ID NO: 6) encoding the rice EPSPS mutant that contains only mutations G111(96)A and P116(101)S but no mutation K100(85)I was taken as Experiment Group 2.

*E. coli* transformed by the gene (SEQ ID NO: 7) encoding the rice EPSPS mutant II provided in Example 2 was taken as Experiment Group 3 (the encoded rice EPSPS mutant II contained three mutations: K100(85)I, G111(96)A and P116(101)S).

E. coli transformed by the gene (SEQ ID NO: 1, which encoded the wild-type rice EPSPS represented by SEQ ID NO: 2) encoding the wild-type rice EPSPS was taken as a control group.

The glyphosate resistance of the gene encoding the rice EPSPS mutant I and the rice EPSPS mutant I encoded thereby in E. coli, and the glyphosate resistance of the gene encoding the rice EPSPS mutant II and the rice EPSPS mutant II encoded thereby in E. coli were verified by detecting the growth situation of the transformed E. coli in culture media (culture media obtained by adding a certain concentration of antibiotics Spec (Spectinomycin), Gen (Gentamycin), Amp (Ampicillin) and glyphosate of different concentrations, with M9 as a basal culture medium) containing different glyphosate concentrations (0 mM, 1 mM, 10 mM, and 50 mM).

In the above, the M9 basal culture medium can be prepared by the following method:

5×M9 salt solution: 6.78 g of $Na_2HPO_4$, 3.0 g of $KH_2PO_4$, 0.5 g of NaCl, and 1.0 g of $NH_4Cl$ were weighed, added with $ddH_2O$ to 200 ml, and subjected to high-temperature and high-pressure sterilization treatment;

20% glucose: 20 g of glucose was weighed, added with 80 ml of $ddH_2O$ for dissolving, diluted to 100 ml, and subjected to filtration and sterilization treatments;

1.0 M $MgSO_4$: 24.6 g of $MgSO_4$-$7H_2O$ was weighed, dissolved with 80 ml of $ddH_2O$, diluted to 100 ml, and subjected to sterilization treatment;

1.0 M $CaCl_2$: 11.1 g of $CaCl_2$ was weighed, dissolved with 80 ml of $ddH_2O$, diluted to 100 ml, and subjected to sterilization treatment; and 1000 ml of the M9 basal culture media were prepared by adding $ddH_2O$ to 200 ml of 5×M9 salt solution, 20 ml of 20% glucose, 2 ml of 1.0 M $MgSO_4$ and 0.1 ml of 1.0 M $CaCl_2$) to make up to 1000 ml.

In the above, the E. coli used was double knockout E. coli, namely, EPSPS defective E. coli (E. coli DH5α with EPSPS gene and C-P Lyase gene being knocked out, named as EDCE, wherein for a preparation method thereof, reference can be made to a Chinese invention patent with the filing number CN2016103256926).

The detection method is a method commonly known in the art, and is briefly described as follows: synthesizing the gene encoding the rice EPSPS mutant by using a chemical synthesis method, introducing enzyme sites (Pac1 and Sbf1) at two ends thereof, connecting to an expression vector (for example, a pADV5 vector, the structure of which is shown in FIG. 4) that had undergone the same restriction enzyme digestion treatment under the action of ligase after restriction enzyme digestion, then transforming double knockout E. coli, picking positive colonies after verification, inoculating the positive colonies to a culture medium containing glyphosate for growth, and observing the growth situation.

Results are as shown in FIG. 1 (wherein R0 is a control group, R1 is Experiment Group 1, R2 is Experiment Group 2, and R3 is Experiment Group 3).

In the culture media containing 0 mM glyphosate, all of the EPSPS defective E. coli in the control group and Experiment Groups 1-3 could grow, indicating that all EPSPS proteins (SEQ ID NO: 2, SEQ ID NO: 4, SEQ ID NO: 6, SEQ ID NO: 8) in the experiment groups and the control group had normal EPSPS enzyme activity.

In the culture media containing 1 mM glyphosate, the control group (R0) grew slowly, and Experiment Group 1 (R1) obviously grew better than the control group (R0), indicating that the glyphosate-resistant capacity of the EPSPS mutant containing single mutation K100(85)I was obviously superior to that of the wild-type EPSPS.

Both Experiment Group 2 (R2) and Experiment Group 3 (R3) could grow in the culture media containing 10 mM glyphosate, but the growth of Experiment Group 3 (R3) was obviously superior to that of Experiment Group 2 (R2), and only Experiment Group 3 (R3) could grow in the culture media containing 50 mM glyphosate, indicating that the site mutation K100(85)I could further substantially improve the glyphosate resistance on the basis of the glyphosate resistance provided by the site mutations G111(96)A and P116(101)S.

The above results show that the single mutation K100(85)I could endow the rice EPSPS mutant with glyphosate resistance, and it has the property of enhancing the glyphosate resistance after being combined with mutations G111(96)A and P116(101)S.

Example 6

*E. coli* transformed by the gene (SEQ ID NO: 9, which encoded the wild-type maize EPSPS represented by SEQ ID NO: 10) encoding the wild-type maize EPSPS was taken as a control group.

*E. coli* transformed by the gene (SEQ ID NO: 11, which encoded SEQ ID NO: 12) encoding the maize EPSPS mutant I that contained only a single mutation K94(85)I, was taken as Experiment Group 1.

*E. coli* transformed by the gene (with a nucleotide sequence represented by SEQ ID NO: 13, and the amino acid sequence of the encoded three-mutation maize EPSPS mutant is represented by SEQ ID NO: 14) encoding the maize EPSPS mutant that contained only three mutations G105(96)A, P110(101)S and K207(194)R but no mutation K94(85)I, was taken as Experiment Group 2.

*E. coli* transformed by the gene (SEQ ID NO: 15) encoding the maize EPSPS mutant (containing four mutations: K94(85)I, G105(96)A, P110(101)S and K207(194)R) provided in Example 3 was taken as Experiment Group 3.

The glyphosate resistance of the gene encoding the maize EPSPS mutant and the maize EPSPS mutant encoded thereby in the *E. coli* was verified by detecting the growth situation of the transformed *E. coli* in culture media containing different glyphosate concentrations (0, 1, 20, 50 mM). In the above, the *E. coli* used is double knockout *E. coli.*

Results are as shown in FIG. 2 (wherein Z0 represents a control group, Z1 represents Experiment Group 1, Z2 represents Experiment Group 2, and Z3 represents Experiment Group 3).

In the culture media containing 0 mM glyphosate and 1 mM glyphosate, all the experiment groups and the control group could grow normally, indicating that EPSPS proteins in the experiment groups and the control group had normal EPSPS enzyme activity; but the growth of Experiment Group 1 (Z1) was obviously superior to that of control group (Z0), and the growth of *E. coli* in Experiment Group 3 (Z3) was obviously superior to that of Experiment Group 2 (Z2), indicating that the mutation K94(85)I provided higher EPSPS enzyme activity.

In the culture media containing 1 mM glyphosate, the growth of the control group (Z0) was weak, and the growth of Experiment Group 1 (Z1) was obviously superior to that of the control group (Z0), indicating that the glyphosate resistance of the EPSPS mutant I containing single mutation K94(85)I was obviously superior to that of the wild-type EPSPS.

Experiment Group 2 (Z2) and Experiment Group 3 (Z3) both could grow in culture media containing 20 mM glyphosate, but the growth of Experiment Group 3 (Z3) was obviously superior to that of Experiment Group 2 (Z2), and only Experiment Group 3 (Z3) could grow in the culture media containing 50 mM glyphosate, indicating that the site mutation K94(85)I could further substantially improve the glyphosate resistance on the basis of the glyphosate resistance provided by the site mutations G105(96)A, P110 (101)S and K207(194)R.

The above results further indicate that the single mutation K94(85)I combined with mutations G105(96)A, P110(101)S and K207(194)R has the property of enhancing the glyphosate resistance.

Example 7

E. coli transformed by the gene (SEQ ID NO: 17, which encoded the wild-type soybean EPSPS represented by SEQ ID NO: 18) encoding the wild-type soybean EPSPS was taken as a control group.

E. coli transformed by the gene (SEQ ID NO: 19, wherein the amino acid sequence of the single-mutation soybean EPSPS mutant encoded thereby is represented by SEQ ID NO: 20) encoding the single-mutation soybean EPSPS mutant, which contained only mutation K98(85)T but no mutation P114(101)S, was taken as Experiment Group 1.

E. coli transformed by the gene (with a nucleotide sequence represented by SEQ ID NO: 21, wherein an amino acid sequence of the single-mutation soybean EPSPS mutant encoded thereby was represented by SEQ ID NO: 22) encoding the single-mutation soybean EPSPS mutant, which contained only mutation P114(101)S but no mutation K98 (85)T, was taken as Experiment Group 2.

E. coli transformed by the gene (SEQ ID NO: 23) encoding the soybean EPSPS mutant (containing two mutations K98(85)T and P114(101)S) provided in Example 4 was taken as Experiment Group 3.

The glyphosate resistance of the gene encoding the soybean EPSPS mutant and the soybean EPSPS mutant encoded thereby in the E. coli was verified by detecting the growth situation of the E. coli in culture media containing different glyphosate concentrations (0, 1, 10 mM). In the above, the E. coli used is double knockout E. coli.

Results are as shown in FIG. 3 (wherein G0 represents a control group, G1 represents Experiment Group 1, G2 represents Experiment Group 2, and G3 represents Experiment Group 3): in the culture media containing 0 mM glyphosate, all of the experiment groups and the control group could grow normally, indicating that EPSPS proteins of the experiment groups and the control group had normal EPSPS enzyme activity.

In the culture media containing 1 mM glyphosate, the control group (G0) substantially could not grow, the growth of Experiment Group (G1) was obviously superior to the control group (G0), indicating that the glyphosate resistance of the soybean EPSPS mutant containing a single mutation K98(85)T was obviously superior to that of the wild-type soybean EPSPS.

Experiment Group 2 (G2) and Experiment Group 3 (G3) both could grow in the culture media containing 20 mM glyphosate, but the growth of Experiment Group 3 (G3) was superior to that of Experiment Group 2 (G2), indicating that the site mutation K98(85)T could further improve the glyphosate resistance on the basis of the glyphosate resistance provided by the site mutation P114(101)S.

The results further indicate that the single mutation K98 (85)T had glyphosate resistance, and had the property of enhancing the glyphosate resistance after being combined with the mutation P114(101)S.

Example 8

A method for detecting the glyphosate resistance of the G1 soybean EPSPS mutant (SEQ ID NO: 20), G2 soybean EPSPS mutant (SEQ ID NO: 22) and G3 soybean EPSPS mutant (SEQ ID NO: 24) provided in Example 7, the R1 rice EPSPS mutant (SEQ ID NO: 4) provided in Example 5, and the Z1 maize EPSPS mutant (SEQ ID NO: 12) provided in Example 6 in the transgenic rice is as follows:

The plasmids (containing the EPSPS mutant gene) of the monoclonal resistant bacteria of pADV5-EPSPS in Examples 1-7 were extracted by a conventional method, followed by double enzyme digestion by Pac1 and BstEII, the small fragments were collected, and then the small fragments were ligated, using T4 DNA ligase, to the pGVP1 vectors that had undergone the same double enzyme digestion, to obtain a pGVP1-EPSPS vector having a structure as shown in FIG. 8.

EHA105 (Agrobactrium tumefaciens) competent cells were transformed by the pGVP1-EPSPS vector, and single colonies were picked up to perform bacterial colony PCR detection to identify positive strains; then the positive strains were inoculated into 1 mL of YEP culture medium containing 50 μg·mL$^{-1}$ kanamycin and 50 μg·mL$^{-1}$ rifampin to propagate, and then preserved at −80° C., or used for subsequent experiment.

Rice Transformation:

400 μl of bacterium containing the target gene vector preserved at −80° C. was added to a culture dish of solid culture media containing YEP+50 μg/mL rifampin+50 μg/mL kanamycin, and cultured in the dark at 28° C. for 24 hours, then this bacterium was added to an infection culture medium, and this bacterial solution was adjusted to OD=0.2 as an infection liquid.

Sterilization and pre-culturing: mature rice (Nipponbare) seeds were manually shelled, and full seeds without bacterial plaque were selected, and sterilized according to following steps: putting the seeds into a 50 ml sterile centrifuge tube, adding 70% alcohol for disinfection for 30 seconds, pouring out the alcohol, and cleaning the seeds once with sterile water; adding 10-20 ml of 2.6% sodium hypochlorite solution for soaking and sterilizing for 20 min, pouring out the sodium hypochlorite solution, and soaking and cleaning the seeds with sterile water for 6-7 times, 3 minutes each time.

Induction and subculturing: the seeds were put on sterile filter paper for drying, and mature embryos were put in an induction culture medium with 12 embryos in each dish; the culture dishes were sealed with a sealing film after the operation was finished, the mature embryos were cultured in the dark at 30° C. for 21-28 days, calluses were transferred into a fresh culture medium, and continuously cultured for about 7-14 days, and spherical calluses with a size of 1-2 mm were taken as infection receptors.

Infection and Co-Culturing:

the calluses were inoculated into a centrifuge tube or a culture cup, the prepared Agrobacterium tumefaciens suspension liquid was added for infection for 10 minutes, wherein the calluses were shaken several times; the bacterial solution was poured out, the calluses were taken out, and placed on sterile filter paper to suck out the surface bacterial solution (about 30 minutes); and the calluses were put on sterile filter paper in a culture dish, and cultured in the dark at 25° C. for 2-3 days.

Recovery culturing: the calluses having undergone co-culturing were inoculated in a recovery culture medium, and cultured in the dark at 30° C. for 5-7 day. First round of screening: the calluses were transferred to screening culture media 1 (S1) and cultured in the dark at 30° C. for 14 days.

Second round of screening: the calluses were then transferred to screening culture media 2 (S2) and cultured in the dark at 30° C. for 14 days.

First round of differentiation: the screened resistant calluses were transferred into differentiation culture medium, illuminated in light at 30° C. for 19 hours, and cultured for about 21 days. Second round of differentiation: newborn young buds were picked out and transferred to a new differentiation culture medium, and continuously cultured for about 21 days.

When growing to about 2 cm, newborn seedlings were transferred to a rooting culture medium to be cultured in light (16/8 h) at 30° C. for 3~4 weeks, after roots were induced and the seedlings grew to 7~10 cm, the seedlings were taken out from the culture medium, to wash off the culture medium contaminated on the roots, and the seedlings were transplanted to a growing tray, and continuously cultured for about 10 d, and then transferred to greenhouse or field.

Formula of the Culture Media:

Induction culture medium: NB BasaL Medium [N6 macronutrients+MS iron salt solution+B5 micronutrients and organic nutrients]+hydrolyzing casein 0.3 g/L+L-proline 2.787 g/L+sucrose 30 g/L+2,4-D 4 mg/L+agar 8 g/L, pH5.8.

Infection culture medium: NB BasaL Medium [N6 macronutrients+MS iron salt solution+B5 micronutrients and organic nutrients]+L-proline 0.7 g/L+sucrose 68.4 g/L+ glucose 36 g/L+2,4-D 2 mg/L pH5.2 (in small pot at 115° C.), AS 20 mg/L added when in use.

Co-culturing culture medium: NB BasaL Medium [N6 macronutrients+MS iron salt solution+B5 micronutrients and organic nutrients]+hydrolyzing casein 0.3 g/L+L-proline 2.787 g/L+sucrose 30 g/L+2,4-D 1 mg/L pH5.2, AS 20 mg/L added when in use.

Recovery culture medium: NB BasaL Medium [N6 macronutrients+MS iron salt solution+B5 micronutrients and organic nutrients]+glutamine 0.2 g/L+L-proline 2.787 g/L+sucrose 30 g/L+2,4-D 4 mg/L+agar 8 g/L, pH5.8. Cefotaxime (100 mg/L)+Timentin 100 mg/L+Vancomycin 50 mg/L were added after sterilization.

Screening culture medium 1 (S1): NB BasaL Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH5.8. Cefotaxime (100 mg/L)+Timentin 100 mg/L+Vancomycin 50 mg/L were added after sterilization. Screening agent (Glyphosate 400 mg/L, or hygromycin 50 mg/L) was added.

Screening culture medium 2 (S2): NB BasaL Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH5.8. Cefotaxime (100 mg/L)+Timentin 100 mg/L+Vancomycin 50 mg/L were added after sterilization. Screening agent (Glyphosate 50-400 mg/L, or hygromycin 30 mg/L) was added.

Differentiation culture medium (F): MS BasaL Medium [MS macronutrients+iron salt solution+micronutrients and organic nutrients]+glutamine 0.2 g/L+sucrose 30 g/L+sorbitol 30 g/L+agar 8 g/L pH5.8. Cefotaxime 200 mg/L+KT 2 mg/L+NAA 0.02 mg/L+GLyphosate 1-5 mg/L were added after sterilization.

Screening agent (Glyphosate 1-5 mg/L, or hygromycin 20 mg/L) was added.

Rooting culture medium: 1/2 MS BasaL Medium [MS macronutrients+iron salt solution+micronutrients and organic nutrients]+inositol 0.1 g/L+sucrose 30 g/L+agar 8 g/L, pH5.8. Cefotaxime 100 mg/L and NAA 0.2 mg/L were added after sterilization.

Detection of Transgenic Plants:

The rice plants transformed by the EPSPS mutant gene were detected using the PCR method, and forward and reverse detecting primers were designed according to the pGVP1-EPSPS vector sequence and the rice reference gene, and primer sequences are as follows:

For parts of sequences of the vector:

```
CaMV15:
                                      (SEQ ID NO: 26)
    5'-GGTGGCTCCTACAAATGCCATC-3';

CTS3:
                                      (SEQ ID NO: 27)
    5'-GAGCCAATTAACGTCATCCCAC-3';
``` an amplified fragment had a size of 452 bp;

For the rice reference gene:

```
OsF:
                                      (SEQ ID NO: 28)
    5'-GCTTCTGACCAGCCCATTATTCTGC-3';

OsR:
                                      (SEQ ID NO: 29)
    5'-CCCTCAAGGGTAAGCTCATCTCTCTTC-3';
``` an amplified fragment had a size of 629 bp.

Genomic DNAs of the rice plants transformed by the pGVP1-EPSPS gene were extracted respectively, and homogenized to 100 ng/μL.

A PCR detection system: 10 μL 2×TsINGKe, 2 μL of a primer mixture (10 μmol/L of OsF, OsR, CaMV15, CTS3, 0.5 μL for each), 1 μL of genomic DNA template (100 ng/μL), 7 μL of ddH$_2$O.

A PCR detection procedure: 94° C., 3 min; 94° C., 30 s; 62° C., 30 s; 72° C., 45 s; 30 cycles; 72° C., 10 min; maintained at 12° C.

PCR amplification products underwent 1.5% agarose gel electrophoresis, wherein products having bands at site 452 bp and site 629 bp were transgenic positive tobacco plants.

In the present example, the glyphosate resistance of the EPSPS mutant in transgenic rice plants were verified. An experiment method is as follows:

The transgenic rice seedlings transplanted were uniformly arranged in a same experiment area (preventing leaves from overlapping). The areas occupied by the experiment groups and the control group were calculated, and according to the areas, glyphosate was sprayed at a 1× dosage of 1060 g/hectare (0.106 g/m$^2$). 2× dosage was 2120 g/hectare, 5× dosage was 5300 g/hectare, and 20× dosage was 21200 g/hectare.

Commercially available Roundup® 41% ammonium glyphosate was used. Roundup® ammonium glyphosate with corresponding volumes was taken according to the above sprayed concentrations, then diluted with 20 times of volume of water, and then uniformly sprayed on the plants in the experiment groups and the control group. After leaf surfaces were dry, the plants were moved into greenhouse or outdoor to cultivate.

Statistical standards used to evaluate glyphosate resistance were as follows: if a plant was not damaged by glyphosate at all and grew normally, it was considered as a plant with high glyphosate resistance, denoted by "+++"; if a plant showed leaves yellowed to some extent and grew slightly slowly, it was considered as a plant with medium glyphosate resistance, denoted by "++"; if a plant had some leaves withered and grew quite slowly, it was considered as a plant with low glyphosate resistance, denoted by "+"; if a plant withered and died, it was considered as a plant with no glyphosate resistance (having no glyphosate resistance), denoted by "−".

After the glyphosate was sprayed at the 1× dosage, growth states of the plants in each group were observed and recorded on a 10$^{th}$ day, and glyphosate was sprayed to the survived plants at the 2× dosage. The growth states of the plants in each group were observed and recorded 10 days later, and glyphosate was sprayed to the survived plants at the 5× dosage. The growth states of the plants in each group were observed and recorded 10 days later, and glyphosate was sprayed to the survived plants at the 20× dosage. The growth states of the plants in each group were observed and recorded 10 days later, and results are shown in Table 1, wherein corresponding numbers of plants denoted by −, +, ++ and +++ are listed, and "%++&+++" is percentage of plant having medium and high glyphosate resistance to the total number of plants observed. Results are shown in Table 1.

tance to glyphosate at the 1× dosage, but all rice seedlings containing the soybean EPSPS mutant G2 died at the 2× dosage, and 19.4% of the rice seedlings containing the soybean EPSPS mutant G3 had medium glyphosate resistance, indicating that the soybean EPSPS site mutation K98(85)T could quite obviously further improve the glyphosate resistance on the basis of the glyphosate resistance provided by the site mutation P114(101)S.

After the glyphosate was sprayed at the 1× dosage, all the rice transformed by the wild-type rice EPSPS R0 had no resistance, one was seriously damaged, and all the others died, but the glyphosate resistance of the rice seedlings transformed by the rice EPSPS mutant R1 was obviously superior to that of the rice seedlings transformed by R0, 88.9% of the rice seedlings had medium glyphosate resistance or high glyphosate resistance, and even at the 2× and 5× glyphosate dosages, 27.8% and 11.1% of the rice seedlings transformed by R1 still had medium glyphosate resistance or high glyphosate resistance, indicating that the glyphosate resistance of the rice EPSPS single mutant containing K100(85)I was obviously superior to that of the wild type.

After the glyphosate was sprayed at the 1× dosage, although a minority of the rice seedlings transformed by the wild-type maize EPSPS Z0 survived, they were seriously damaged, with no plant having medium or high glyphosate resistance, while the glyphosate resistance of the rice seedlings transformed by the maize EPSPS mutant Z1 was obviously superior to that of Z0, 10.5% of the rice seedlings had medium glyphosate resistance or high glyphosate resistance, and at the 2× and 5× glyphosate dosages, no rice

TABLE 1

| | resistance | G0 | G1 | G2 | G3 | R0 | R1 | Z0 | Z1 |
|---|---|---|---|---|---|---|---|---|---|
| 1X dosage | − | 36 | 29 | 3 | 16 | 30 | 2 | 16 | 16 |
| | + | 0 | 6 | 6 | 1 | 1 | 0 | 4 | 1 |
| | ++ | 0 | 2 | 5 | 9 | 0 | 0 | 0 | 2 |
| | +++ | 0 | 0 | 3 | 5 | 0 | 16 | 0 | 0 |
| | % ++&+++ | 0.0 | 5.4 | 47.1 | 45.2 | 0.0 | 88.9 | 0.0 | 10.5 |
| 2X dosage | − | 36 | 33 | 17 | 20 | 31 | 8 | 20 | 16 |
| | + | 0 | 4 | 0 | 5 | 0 | 5 | 0 | 3 |
| | ++ | 0 | 0 | 0 | 6 | 0 | 4 | 0 | 0 |
| | +++ | 0 | 0 | 0 | 0 | 0 | 1 | 0 | 0 |
| | % ++&+++ | 0.0 | 0.0 | 0.0 | 19.4 | 0.0 | 27.8 | 0.0 | 0.0 |
| 5X dosage | − | 36 | 37 | 17 | 21 | 31 | 13 | 20 | 17 |
| | + | 0 | 0 | 0 | 10 | 0 | 3 | 0 | 2 |
| | ++ | 0 | 0 | 0 | 0 | 0 | 2 | 0 | 0 |
| | +++ | 0 | 0 | 0 | 0 | 0 | 0 | 0 | 0 |
| | % ++&+++ | 0.0 | 0.0 | 0.0 | 0.0 | 0.0 | 11.1 | 0.0 | 0.0 |
| 20X dosage | − | 36 | 37 | 17 | 28 | 31 | 16 | 20 | 19 |
| | + | 0 | 0 | 0 | 3 | 0 | 2 | 0 | 0 |
| | ++ | 0 | 0 | 0 | 0 | 0 | 0 | 0 | 0 |
| | +++ | 0 | 0 | 0 | 0 | 0 | 0 | 0 | 0 |
| | % ++&+++ | 0.0 | 0.0 | 0.0 | 0.0 | 0.0 | 0.0 | 0.0 | 0.0 |

It can be seen from the results of Table 1 that after the glyphosate was sprayed at the 1× dosage, all the rice transformed by the wild-type soybean EPSPS G0 had no resistance and died, but the glyphosate resistance of the rice seedlings transformed by the soybean EPSPS mutant G1 was obviously superior to that of G0, 6.4% of the rice seedlings had medium glyphosate resistance or high glyphosate resistance, and some of the rice seedlings transformed by G1 still survived under the 2× glyphosate dosage, indicating that the soybean EPSPS single mutant containing K98(85)T had the glyphosate resistance obviously superior to that of the wild type.

The rice transformed by the soybean EPSPS mutant G2 and the soybean EPSPS mutant G3 both had certain resistransformed by the wild-type maize EPSPS Z0 survived, but some of the rice seedlings transformed by the maize EPSPS mutant Z1 survived, respectively, indicating that the glyphosate resistance of the maize EPSPS single mutant containing K94(85)I was obviously superior to that of the wild type.

The above results sufficiently indicate that compared with the E. coli EPSPS sequence, the amino acid sequence of the plant EPSPS mutant containing a mutation K851 corresponding to the site 85 of the E. coli EPSPS can endow the plant EPSPS mutant with the glyphosate resistance in the plant or improve the glyphosate resistance of the plant EPSPS mutant in the plant.

To sum up, compared with the wild-type plant EPSPS, for example, the wild-type rice EPSPS, the wild-type maize EPSPS, and the wild-type soybean EPSPS, the plant EPSPS mutant (the single-mutation rice EPSPS mutant represented by SEQ ID NO: 3, the single-mutation maize EPSPS mutant represented by SEQ ID NO: 12, the single-mutation soybean EPSPS mutant represented by SEQ ID NO: 20 and the multi-mutation rice EPSPS mutant represented by SEQ ID NO: 8, the multi-mutation maize EPSPS mutant represented by SEQ ID NO: 16, and the multi-mutation soybean EPSPS mutant represented by SEQ ID NO: 24) and the gene encoding the plant EPSPS mutant provided in the present disclosure have higher glyphosate resistance and complete bio-enzyme activity.

Besides, the plant EPSPS mutant and the gene encoding the plant EPSPS mutant provided in the present disclosure, derived from rice, maize, soybean per se rather than microorganisms, are applicable to transform various types of plant, for example, rice, tobacco, soybean, maize, cotton, sorghum, and wheat, which has a broader application range. Meanwhile, according to the sequence of the gene encoding the plant EPSPS mutant provided in the present disclosure, they can be used for cultivating new glyphosate-resistant rice species (non-transgenic method), to obtain conventional glyphosate-resistant non-transgenic species, which improves the degree of public acceptance of new species.

The above-mentioned are merely for preferred examples of the present disclosure and not used to limit the present disclosure. For one skilled in the art, various modifications and changes may be made to the present disclosure. Any modifications, equivalent substitutions, improvements and so on made within the spirit and principle of the present disclosure, should be covered within the scope of protection of the present disclosure.

What is claimed is:

1. A plant 5-enolpyruvylshikimate-3-phosphate synthase (EPSPS) mutant polypeptide, wherein compared with a *E. coli* EPSPS, an amino acid sequence of the plant EPSPS mutant polypeptide contains a mutation corresponding to a site 85 of the *E. coli* EPSPS, wherein the *E. coli* EPSPS has an amino acid sequence represented by SEQ ID NO. 25, and the plant EPSPS mutant polypeptide has the amino acid sequence represented by SEQ ID NO. 4, SEQ ID NO. 8, SEQ ID NO. 16, or SEQ ID NO. 24.

2. The plant EPSPS mutant polypeptide according to claim 1, wherein the amino acid sequence of the plant EPSPS mutant polypeptide contains a mutation of K to T or K to I corresponding to the site 85 of the *E. coli* EPSPS.

3. The plant EPSPS mutant polypeptide according to claim 1 wherein the amino acid sequence of the plant EPSPS mutant polypeptide further contains one of following mutations corresponding to the *E. coli* EPSPS: G96A, P101S and K194R or any combination thereof.

4. The plant EPSPS mutant polypeptide according to claim 1 wherein the plant EPSPS mutant polypeptide is derived from rice, and the amino acid sequence of the plant EPSPS mutant polypeptide contains the following mutations corresponding to the *E. coli* EPSPS: K85I, G96A and P101S.

5. The plant EPSPS mutant polypeptide according to claim 1 wherein the plant EPSPS mutant polypeptide is derived from maize, and the amino acid sequence of the plant EPSPS mutant polypeptide contains the following mutations corresponding to the *E. coli* EPSPS: K85I, G96A, P101S and K194R.

6. The plant EPSPS mutant polypeptide according to claim 1 wherein the plant EPSPS mutant polypeptide is derived from soybean, and the amino acid sequence of the plant EPSPS mutant polypeptide contains the following mutations corresponding to the *E. coli* EPSPS: K85T and P101S.

7. A polynucleotide encoding the plant EPSPS mutant polypeptide according to claim 1.

* * * * *